(12) United States Patent
Hart et al.

(10) Patent No.: US 11,844,719 B2
(45) Date of Patent: Dec. 19, 2023

(54) BREATHING ASSIST DEVICE

(71) Applicant: Open Airway Dental Solutions Ltd., Toronto (CA)

(72) Inventors: Christopher Patrick Hart, Indooroopilly (AU); Vu Thua Nguyen, Indooroopilly (AU); Neil Lawrence Anderson, Indooroopilly (AU); Darren Fraser, Indooroopilly (AU); Michael Leigh Slater, Indooroopilly (AU); Stefan Gulizia, Indooroopilly (AU)

(73) Assignee: Open Airway Dental Solutions Ltd., Toronto (CA)

( * ) Notice: Subject to any disclaimer, the term of this patent is extended or adjusted under 35 U.S.C. 154(b) by 440 days.

(21) Appl. No.: 16/814,355

(22) Filed: Mar. 10, 2020

(65) Prior Publication Data
US 2020/0206020 A1    Jul. 2, 2020

Related U.S. Application Data

(63) Continuation of application No. 15/300,865, filed as application No. PCT/AU2015/050144 on Mar. 31, 2015, now Pat. No. 10,632,010.

(30) Foreign Application Priority Data

Apr. 1, 2014 (AU) ................................ 2014901181
May 6, 2014 (AU) ................................ 2014901655
Aug. 8, 2014 (AU) ................................ 2014903083

(51) Int. Cl.
*A61F 5/56*       (2006.01)
*A61M 16/10*   (2006.01)
(Continued)

(52) U.S. Cl.
CPC ............ *A61F 5/566* (2013.01); *A61M 16/107* (2014.02); *A61M 16/1045* (2013.01);
(Continued)

(58) Field of Classification Search
CPC ....... A61F 5/566; A61F 5/56; A61F 2005/563; A61F 5/58; A61F 5/0102;
(Continued)

(56) References Cited

U.S. PATENT DOCUMENTS 2,521,039 A * 9/1950 Carpenter ............ A63B 71/085
                                                          128/861
2,820,457 A     1/1958 Phillips
(Continued)

FOREIGN PATENT DOCUMENTS

CN          1217640 A       5/1999
CN          2494659 Y       6/2002
(Continued)

OTHER PUBLICATIONS

Notice of Allowance dated Dec. 1, 2022 in U.S. Appl. No. 16/003,558.
(Continued)

*Primary Examiner* — Tarla R Patel
(74) *Attorney, Agent, or Firm* — Heer Law; Christopher D. Heer

(57) ABSTRACT

Apparatus for providing breathing assistance, the apparatus including a body for positioning within an oral cavity of a user, the body defining at least one first opening for allowing airflow between lips of the user, two second openings provided in the oral cavity to allow air flow into and out of a posterior region of the oral cavity and two channels, each channel connecting a respective second opening to the at least one first opening and each channel passing at least one of at least partially along the buccal cavity and at least partially between the teeth to thereby provide an airway for
(Continued)

the user, the airway at least partially bypassing the nasal passage and acting to replicate a healthy nasal passage and pharyngeal space.

21 Claims, 14 Drawing Sheets

(51) Int. Cl.
*A61M 16/20* (2006.01)
*A63B 71/08* (2006.01)

(52) U.S. Cl.
CPC ........... *A61M 16/20* (2013.01); *A63B 71/085* (2013.01); *A61M 2207/00* (2013.01); *A63B 2071/086* (2013.01)

(58) Field of Classification Search
CPC ...... A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A63B 71/085; A63B 2071/086; A63B 2017/088; A61M 16/1045; A61M 16/107; A61M 16/20; A61M 2207/00; A61C 7/08; A61C 19/063; A61B 5/4547; A61B 5/4552; A61B 5/4557; A61B 5/682; A61B 5/0534

See application file for complete search history.

(56) References Cited

U.S. PATENT DOCUMENTS

| | | | |
|---|---|---|---|
| 4,169,473 A | 10/1979 | Samelson | |
| 4,170,230 A | 10/1979 | Nelson | |
| 4,289,127 A | 9/1981 | Nelson | |
| 4,304,227 A | 12/1981 | Samelson | |
| 4,676,240 A | 6/1987 | Gardy | |
| 5,067,896 A | 11/1991 | Korn | |
| 5,092,346 A | 3/1992 | Hays et al. | |
| 5,313,960 A | 5/1994 | Tomasi | |
| 5,465,734 A | 11/1995 | Alvarez et al. | |
| 5,537,994 A | 7/1996 | Thornton | |
| 5,792,067 A | 8/1998 | Karell | |
| 5,941,246 A | 8/1999 | Roopchand | |
| 5,954,048 A | 9/1999 | Thornton | |
| 5,983,892 A | 11/1999 | Thornton | |
| 6,055,989 A | 5/2000 | Rehnke | |
| 6,374,824 B1 | 4/2002 | Thornton | |
| 6,474,339 B1 | 11/2002 | Grosbois et al. | |
| 8,931,487 B2 | 1/2015 | Razmovski | |
| 9,375,344 B2* | 6/2016 | de Heer | A61B 5/411 |
| 2002/0139375 A1 | 10/2002 | Kulick | |
| 2004/0103905 A1* | 6/2004 | Farrell | A61C 7/08 |
| | | | 128/861 |
| 2004/0194787 A1 | 10/2004 | Miller | |
| 2005/0081859 A1 | 4/2005 | Scarberry et al. | |
| 2005/0103331 A1 | 5/2005 | Wedemeyer | |
| 2005/0150504 A1 | 7/2005 | Heeke et al. | |
| 2006/0166157 A1 | 7/2006 | Rahman et al. | |
| 2006/0169289 A1 | 8/2006 | Zacco | |
| 2006/0174897 A1 | 8/2006 | Sarkisian | |
| 2006/0219250 A1 | 10/2006 | Farrell | |
| 2007/0235037 A1 | 10/2007 | Thornton | |
| 2008/0216843 A1 | 9/2008 | Jiang | |
| 2008/0233531 A1 | 9/2008 | Raby et al. | |
| 2008/0257358 A1 | 10/2008 | Stern et al. | |
| 2009/0120446 A1 | 5/2009 | Vaska et al. | |
| 2009/0241969 A1 | 10/2009 | Walker | |
| 2010/0043804 A1 | 2/2010 | Razmovski | |
| 2010/0132700 A1 | 6/2010 | Filipi et al. | |
| 2010/0132720 A1 | 6/2010 | Razmovski | |
| 2010/0152599 A1 | 6/2010 | DuHamel et al. | |
| 2010/0163043 A1 | 7/2010 | Hart et al. | |
| 2010/0311003 A1 | 12/2010 | Kozlov | |
| 2011/0220124 A1 | 9/2011 | Vaska et al. | |
| 2011/0226261 A1* | 9/2011 | Hernandez | A61F 5/566 |
| | | | 128/848 |
| 2011/0232652 A1 | 9/2011 | Evendowski et al. | |
| 2012/0143003 A1 | 6/2012 | Anca et al. | |
| 2012/0145166 A1 | 6/2012 | Fallon et al. | |
| 2013/0074851 A1 | 3/2013 | Herman et al. | |
| 2013/0081640 A1 | 4/2013 | Herman et al. | |
| 2013/0236848 A1 | 9/2013 | Arruda | |
| 2014/0130807 A1 | 5/2014 | Hart | |
| 2014/0261450 A1 | 9/2014 | Morehead | |
| 2014/0276171 A1* | 9/2014 | Hestness | A61B 5/097 |
| | | | 600/531 |
| 2014/0290668 A1 | 10/2014 | Thornton et al. | |
| 2014/0350354 A1 | 11/2014 | Stenzler et al. | |
| 2015/0101615 A1 | 4/2015 | Podmore et al. | |
| 2015/0272773 A1 | 10/2015 | Rico et al. | |
| 2018/0207020 A1* | 7/2018 | Hart | A61F 5/566 |

FOREIGN PATENT DOCUMENTS

| | | |
|---|---|---|
| CN | 101264038 A | 9/2008 |
| JP | 2010-09615 A | 2/2010 |
| JP | 2010-142497 A | 7/2010 |
| WO | 2010038171 A1 | 4/2010 |
| WO | 2010141868 A2 | 12/2010 |
| WO | 2012064684 A2 | 5/2012 |
| WO | 2012140021 A2 | 10/2012 |
| WO | 2012155214 A1 | 11/2012 |
| WO | 2013086586 A1 | 6/2013 |
| WO | 2013134235 A1 | 9/2013 |
| WO | 2014110432 A2 | 7/2014 |
| WO | 2014133969 A1 | 9/2014 |
| WO | 2014144717 A2 | 9/2014 |
| WO | 2016057719 A1 | 4/2016 |
| WO | 2017020079 A1 | 2/2017 |

OTHER PUBLICATIONS

Office Action dated Nov. 24, 2020 in Japanese Application No. 2016-560790.
Office Action dated Apr. 29, 2021 in Chinese Application No. 2019109732671.
Int'l Preliminary Report on Patenability dated Oct. 4, 2016 in Int'l Application No. PCT/AU2015/050144.
Int'l Search Report and Written Opinion dated Jun. 29, 2016 in Int'l Application No. PCT/AU2015/050144.
Int'l Search Report and Written Opinion dated Oct. 14, 2016 in Int'l Application No. PCT/AU2016/050696.
Dffice Action dated Oct. 19, 2015 in U.S. Appl. No. 14/118,416, by Hart.
Int'l Search Report dated Jun. 13, 2012 in Int'l Application No. PCT/AU2012/000565.
Examination Report dated Jan. 18, 2016 in AU Application No. 2012255625.
Office Action dated Dec. 15, 2015 in AU Application No. 2012255625.
Extended Search Report dated Oct. 27, 2014 in EP Application No. 12785448.7.
Office Action dated May 27, 2016 in EP Application No. 12785448.7.
Office action dated Nov. 2, 2016 in U.S. Appl. No. 14/118,416, by Hart.
Office Action dated Feb. 27, 2017 in U.S. Appl. No. 14/118,416 by Carreiro.
Examination Report dated May 19, 2017 in AU Application No. 2015240431.
Extended Search Report dated Jul. 31, 2017 in EP Application No. 15773894.9.

(56) References Cited

OTHER PUBLICATIONS

Office Action dated Oct. 19, 2017 in U.S. Appl. No. 14/118,416, by Hart.
Int'l Search Report and Written Opinion dated Jun. 13, 2017 in Int'l Application No. PCT/AU2017/050271.
Roberts et al., "Proper Depth of Placement of Oral Endotracheal Tubes in Adults Prior to Radiographic Confirmation," Academic Emergency Medicine, vol. 2, No. 2, pp. 20-24 (Jan. 1995).
Office Action dated Feb. 27, 2018 in AU Application No. 2017228641.
Int'l Written Opinion dated Apr. 3, 2018 in Int'l Application No. PCT/AU2017/051316.
Int'l Search Report and Written Opinion dated Nov. 17, 2017 in Int'l Application No. PCT/AU2017/051092.
Office Action dated Feb. 6, 2019 in JP Application No. 2016560790.
Office Action dated Sep. 3, 2019 in JP Application No. 2016-560790.

\* cited by examiner

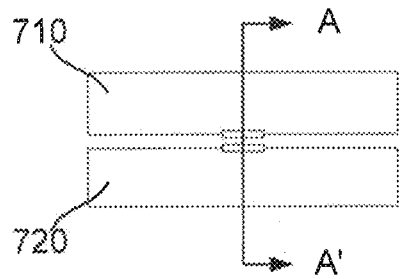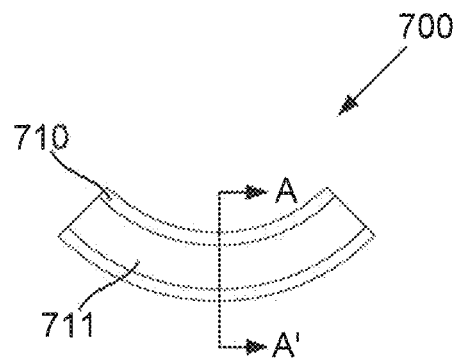
Fig. 7A    Fig. 7B
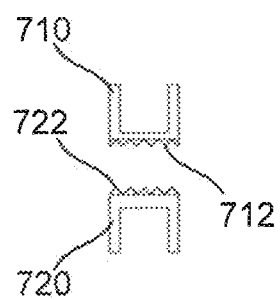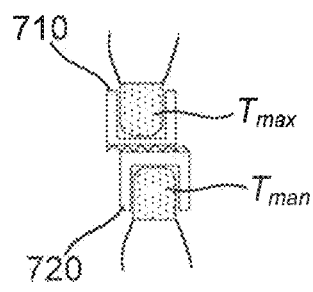
Fig. 7C    Fig. 7D
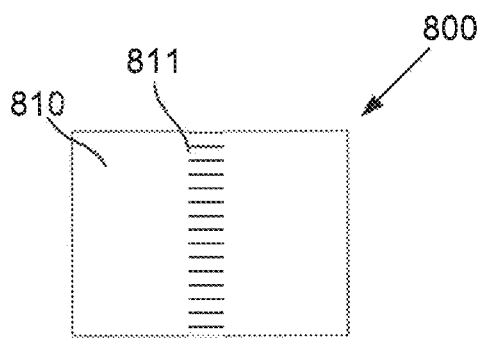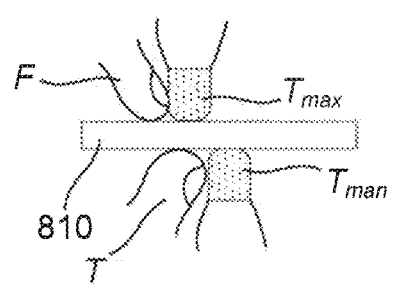
Fig. 8A    Fig. 8B

BREATHING ASSIST DEVICE

CROSS REFERENCE TO RELATED APPLICATIONS

This application is a Continuation of U.S. patent application Ser. No. 15/300,865, filed Sep. 30, 2016, which is a Section 371 of International Application No. PCT/AU2015/050144, filed Mar. 31, 2015, which was published in the English language on Oct. 8, 2015 under International Publication No. WO 2015/149127 A1 and which claims priority under 35 U.S.C. 119(b) to Australian Patent Application No. 2014903083, filed Aug. 8, 2014, Australian Patent Application No. 2014901655, filed May 6, 2014, and Australian Patent Application No. 2014901181, filed Apr. 1, 2014, the disclosures of all of which are incorporated herein by reference.

BACKGROUND OF THE INVENTION

The present invention relates to apparatus for providing breathing assistance, and in particular an apparatus for providing breathing assistance, as well as a method of manufacturing and fitting a breathing assistance apparatus.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Poor quality or ineffective breathing is an issue which can affect the performance of people in their day to day activities either while they are awake and/or when they are asleep. While awake this can be less optimal performance in activities such as sport or even while performing everyday tasks. While asleep breathing disorders can lead to snoring and/or sleep apnea.

Snoring arises due to vibration of soft tissues within the respiratory pathways of an individual, and is typically caused by obstructed air movement during breathing while sleeping. Snoring can arise from a range of different physical causes such as blocked sinuses, and typically occurs when the muscles of the upper throat relax during sleep.

Snoring can also be associated with Obstructive Sleep Apnoea (OSA), which is caused by obstruction of the upper airway and results in repetitive pauses in breathing during normal sleep. Individuals having OSA often suffer from daytime sleepiness and fatigue associated with significant levels of sleep disturbance, whilst a partners sleep patterns are also often disturbed by associated snoring.

Current therapy for treatment of OSA can include lifestyle changes, the use of mechanical devices, such as oral or nasal devices that augment the airway, surgical procedures to enlarge and stabilize the airway during sleep, and continuous or variable positive airway pressure (CPAP, VPAP) devices.

However, surgical procedures can be severe and are not therefore widely used unless absolutely necessary. Whilst CPAP and VPAP devices have had a positive impact, these can be uncomfortable to wear for prolonged time periods, are expensive, and are often noisy, which can in turn lead to additional sleep disturbance. As a result, surgery, VPAP and CPAP treatment have limited application in treating sleep apnoea, and are not generally considered appropriate treatment for snoring.

In terms of other mechanical devices, nasal devices have been used that dilate the nasal airway using traction or splinting. However, these have typically not had much success and can be uncomfortable for a user.

US2004/194787 describes an anti-snoring device that includes a flexible hollow tube for insertion into the user's mouth, having proximal and distal ends and an outer perimeter. The tube includes an extraoral segment at its proximal end, an intraoral segment at its distal end and an intermediate segment extending therebetween. The extraoral and intraoral segments each include at least one opening. The extraoral segment is for extending beyond the user's outer lips, the intermediate segment is of a sufficient length for extending along the buccopharyngeal pathway of the user's mouth, and the intraoral segment is of a sufficient length for extending beyond a retromolar space in the user's mouth, into the oropharynx and terminating between the posterior tongue and the soft palate. The anti-snoring device also includes a stop extending from the outer perimeter of the tube on the intraoral segment for securing the intraoral segment within the user's oropharynx. However, whilst this arrangement can assist in providing an additional airway, and hence reduce snoring and apnoea events, it can be uncomfortable to wear and can move within the mouth during use, which can reduce device effectiveness and in turn lead to additional breathing problems.

US2005/150504 describes a device which is removably insertable in the mouth for facilitating breathing while sleeping which provides a clear unobstructed airway by protrusive positioning of the mandible and/or delivery of pressurized air to the back of the mouth. The device has upper and lower tooth-contacting members and an airway defined between them, and is designed specifically for use with CPAP machines. Consequently, this device can only be used in limited circumstances, where CPAP machines are available, and is only used in the treatment of sleep apnoea.

WO2012/155214 describes apparatus for providing breathing assistance, the apparatus including a body including a recess for receiving teeth of a user to thereby position the body within an oral cavity of the user, a first opening extending beyond lips of a user to allow air from outside the oral cavity to be drawn in through the opening, a second opening provided in the oral cavity to allow air to be directed into a posterior region of the oral cavity and a channel connecting the first and second openings, the channel extending through at least part of a buccal sulcus of the user.

It is also known to provide mouth guards for use during sport. For example, US20130074851 describes a dental appliance including arms disposed about occlusal pad to secure the dental appliance in a removable fashion to the teeth of the user. The occlusal pad is formed from an occlusal pad material transformable between a pliable state and a non-pliable state, in various aspects. Associated methods of use are also disclosed herein.

US20130081640 describes an interchangeable mouthguard component system. The system includes a mouthguard base with a receiving recess positioned within at least a front surface of the base, a securely attachable mouthguard component positioned to fit within the recess, one or more attaching posts positioned on one of the recess or component and one or more holes positioned opposite the posts on either the recess or component. The mouthguard component, when attached, is positioned sufficient to maintain a substantially flush front surface of the base.

However, mouth guards for use in sport are not adapted to provide assistance with breathing and can in some circumstances make breathing more difficult.

WO2012140021 describes a method for generating a virtual orthodontic element for use in manufacturing an orthodontic appliance for a patient. The method comprises obtaining a patient data set for said patient, the patient data set comprises a virtual 3D teeth model, where said virtual 3D teeth model comprises a virtual upper jaw and a virtual lower jaw resembling the upper jaw and lower jaw, respectively, of the patient's mouth, arranging the virtual upper jaw and the virtual lower jaw in an initial relative configuration in a virtual articulator which is able to simulate the articulation between the virtual upper jaw and the virtual lower jaw based at least on motion relative to at least one axis representing the terminal hinge axis of the patient, designing the virtual orthodontic element based on at least a part of the virtual 3D teeth model and the arrangement of the 3D teeth model in the virtual articulator.

However, use of the virtual articulation means that the resulting orthodontic element is not necessarily optimised for patient comfort as this may not take into account the particular articulation of the patient's jaws.

SUMMARY OF THE PRESENT INVENTION

In one broad form the invention seeks to provide apparatus for providing breathing assistance, the apparatus including a body for positioning within an oral cavity of a user, the body defining:
   a) at least one first opening for allowing airflow between lips of the user;
   b) two second openings provided in the oral cavity to allow air flow into and out of a posterior region of the oral cavity; and,
   c) two channels, each channel connecting a respective second opening to the at least one first opening and each channel passing at least one of at least partially along the buccal cavity and at least partially between the teeth to thereby provide an airway for the user, the airway at least partially bypassing the nasal passage and acting to replicate a healthy nasal passage and pharyngeal space, and
   a connector for coupling the body to a mandibular repositioning device.

Typically for a device adapted to be used at rest, each channel has a cross sectional area of at least one of:
   a) at least 10 $mm^2$;
   b) at least 20 $mm^2$;
   c) at least 30 $mm^2$;
   d) at least 40 $mm^2$; and,
   e) at least 50 $mm^2$.

Typically for a device adapted to be used during exercise, each channel has a cross sectional area of at least one of:
   a) at least 20 $mm^2$;
   b) at least 40 $mm^2$;
   c) at least 60 $mm^2$;
   d) at least 80 $mm^2$;
   e) at least 100 $mm^2$;
   f) at least 150 $mm^2$;
   g) at least 200 $mm^2$;
   h) at least 250 $mm^2$; and,
   i) at least 300 $mm^2$.

Typically for a device adapted to be used during exercise, at least one of the first opening and the second openings have a cross sectional area of at least one of:
   a) at least 100 $mm^2$;
   b) at least 140 $mm^2$;
   c) at least 180 $mm^2$;
   d) at least 200 $mm^2$;
   e) at least 220 $mm^2$;
   f) at least 330 $mm^2$;
   g) at least 440 $mm^2$; and,
   h) at least 550 $mm^2$.

Typically for a device adapted to be used at rest, at least one of the first opening and the second openings have a cross sectional area of at least one of:
   a) at least 50 $mm^2$;
   b) at least 70 $mm^2$;
   c) at least 90 $mm^2$;
   d) at least 100 $mm^2$; and,
   e) at least 110 $mm^2$.

Typically the mandibular repositioning device is configured to allow for known increments for bringing the mandible forward.

Typically each channel includes:
   a) a first channel portion extending through the user's buccal cavity; and,
   b) a second channel portion in fluid communication with the first channel portion and extending between the user's maxillary and mandibular teeth.

Typically the first channel portion has substantially semi-elliptical cross section and the second channel portion has a substantially rectangular cross section, the second channel portion extending laterally inwardly from the first channel portion.

Typically at least one of the cross sectional shape and cross sectional area of at least one of the first and second channel portions varies from the first opening to the second opening.

Typically a shape and size of the channels varies in accordance with an anatomy of the oral cavity of the user.

Typically the body defines channel walls, and at least some of the channel walls have a thickness of at least one of:
   a) less than 0.5 mm; and,
   b) approximately 0.3 mm.

Typically the first opening is removably mounted to the body.

Typically the second openings are angled inwardly at least one of:
   a) between 10° and 50°;
   b) between 20° and 40°; and,
   c) approximately 30°.

Typically the second openings are positioned over the last or back tooth on each side of the top jaw.

Typically the body is made of at least one of:
   a) metal;
   b) titanium alloys;
   c) high strength polymers; and,
   d) cobalt chromium alloys.

Typically the body is made using additive manufacturing.

Typically the body is coated with at least one of:
   a) a medical grade polymer;
   b) a medical grade elastomer;
   c) silicone;
   d) polyurethane;
   e) epoxy; and,
   f) parylene.

Alternatively, at least part of the body can be polished using at least one of mechanical and electrochemical polishing.

Typically the apparatus includes at least one insert, the insert being positioned at least partially between the user's teeth and the body in use.

Typically the insert is customised for a user's teeth.

Typically the insert is at least one of removable and replaceable.

Typically the apparatus includes a plurality of inserts for each user, each insert being adapted to provide a different positioning of at least one of the body and the user's teeth.

Typically the insert is adapted to absorb impacts.

Typically the insert is made of at least one of:
 a) metals;
 b) ceramics;
 c) a polymer;
 d) polyvinylsiloxane;
 e) polyurethane; and,
 f) ethylvinylacetate.

Typically each channel directs air through a hammular notch of the user.

Typically the apparatus includes a filter for filtering air flowing through the apparatus.

Typically the filter is positioned within the at least one first opening.

Typically the apparatus includes an exchanger for exchanging at least one of heat and moisture between inhaled and exhaled air.

Typically the exchanger is positioned within the at least one first opening.

Typically the apparatus includes a valve for regulating air flow into and out of the apparatus.

Typically the valve is for resisting outflow of air from the second openings to the first opening.

Typically the body includes a lingual flange for engaging mandibular teeth to thereby maintain mandibular position.

Typically the lingual flange is movably mounted to the body to thereby allow adjustment of a user's mandibular position in known increments.

Typically the apparatus includes an insert having a lingual flange layer extending over at least part of the lingual flange and wherein a thickness of the lingual flange layer is used to adjust the user's mandibular position.

Typically the apparatus includes multiple inserts for each user, and wherein each insert has a different lingual flange layer thickness for adjusting the user's mandibular position in known increments.

Typically the apparatus includes a connector for coupling the body to a mandibular repositioning device.

Typically the mandibular repositioning device includes arms connected to a retainer for engaging the teeth.

Typically lengths of the arms are adjustable.

Typically the apparatus includes mesh extending from the body, the mesh extending past a gum line of the user on at least one of a lingual and labial side to thereby provide protection to teeth of the user in use.

In one broad form the invention seeks to provide a method for manufacturing a breathing assistance apparatus for a user, the method including using additive manufacturing to create a body for positioning within an oral cavity of the user, the body including:
 a) at least one first opening for allowing airflow between lips of the user;
 b) two second openings provided in the oral cavity to allow air flow into and out of a posterior region of the oral cavity;
 c) two channels, each channel connecting a respective second opening to the at least one first opening and each channel passing at least one of at least partially along the buccal cavity and at least partially between the teeth to thereby provide an airway for the user, the airway at least partially bypassing the nasal passage and acting to replicate a healthy nasal passage and pharyngeal space; and
 d) a connector for coupling the body to a mandibular repositioning device.

Typically the body is made of at least one of:
 a) metal;
 b) titanium alloys;
 c) high strength polymers; and,
 d) cobalt chromium alloys.

Typically the method includes applying a coating to the body.

Typically the method coating is applied to inner surfaces of the body.

Typically the method includes applying the coating to the body by at least one of:
 a) dip coating;
 b) spray coating; and,
 c) vapour coating.

Typically the method includes applying primers to the body prior to coating.

Typically the method includes polishing at least part of the body using at least one of mechanical and electrochemical polishing.

Typically the method includes:
 a) obtaining shape information indicative of a shape of the user's oral cavity; and,
 b) manufacturing the breathing assist apparatus using the shape information.

Typically the method includes deriving the shape information from at least one of:
 a) an impression;
 b) a series of photos;
 c) a scan;
 d) a CT scan;
 e) a 3D scan of the user's teeth; and
 f) cone beam imaging.

Typically the series of photos of the patient's mouth or impression taken with a smart phone and the photos are then loaded into a software program to derive a 3D image including an STL file.

Typically the shape information includes dimensions of the oral cavity of the user.

Typically the method includes:
 a) selecting one of a number of standard bodies in accordance with the shape information; and,
 b) using the shape information, at least one of:
  i) modifying the selected standard body; and,
  ii) creating at least one insert.

Typically the method includes:
 a) obtaining template data representing a body design;
 b) modifying the body design using the information derived from the scan;
 c) generating modified template data using the modified body design; and,
 d) manufacturing the body using the modified template data.

Typically the modified template data is in the form of a print file for use in an additive manufacturing machine.

In one broad form the invention seeks to provide a method for use in manufacturing a breathing assistance apparatus for a user, the method including:
 a) determining a desired jaw position;
 b) obtaining shape information indicative of a shape of at least the user's teeth with the user's jaws in the desired jaw position;

c) manufacturing a body of a breathing assistance apparatus at least in part using the shape information; and,
d) manufacturing at least one insert for the desired jaw position of the user, the insert being positioned at least partially between the user's teeth and the body in use.

Typically the method includes, determining the desired jaw position by providing a spacer between the user's teeth.

Typically the spacer is at least one of:
a) the user's tongue;
b) a laminar member including markings indicative of a relative jaw position;
c) top and bottom arch trays that move relative to each other;
d) a folded piece of paper;
e) between 3 mm and 5 mm thick; and,
f) between 3.5 mm and 4.5 mm thick.

Typically the method includes:
a) providing the spacer between the user's teeth;
b) placing the user in a supine position;
c) having the user breathe; and,
d) depending on whether noise is made during breathing, at least one of:
  i) determining the current position to be the desired jaw position; and,
  ii) advancing the lower jaw and repeating steps c) and d).

Typically the method includes determining the shape information by at least one of imaging and scanning at least the user's teeth with the user's jaws at least in the desired jaw position.

Typically the method further includes at least one of imaging and scanning the user's teeth with the jaws in open and closed positions.

Typically the method includes determining the shape information from at least one of:
a) a series of photos;
b) a scan;
c) a CT scan;
d) a 3D scan of the user's teeth; and
e) cone beam imaging.

Typically the images are obtained from at least one of:
a) the user's teeth;
b) an impression and/or bite registration of user's teeth; and,
c) a dental model created from pouring impressions or 3D printing.

Typically the method includes:
a) modifying a print file in accordance with the shape; and,
b) manufacturing the body using the modified print file.

Typically the method includes, manufacturing at least one insert by:
a) applying a resin to the body;
b) moulding the resin based on user's teeth with jaws in the desired jaw position; and,
c) curing the moulded resin.

Typically the method includes:
a) manufacturing a jaw model using the shape information, the jaw model being a model of the user's teeth and jaws; and,
b) moulding the resin using the jaw model.

Typically the method includes at least one of trimming and polishing the cured resin.

Typically a method in certain embodiments includes manufacturing at least one insert using 3D printing from a 3D file.

Typically the insert is printed using at least one of:
a) Polyurethane; and,
b) Ethyl Vinyl Acetate.

Typically the method includes manufacturing at least one insert by:
a) thermoforming a thin sheet of a thermoplastic onto a jaw model;
b) placing the thermoformed sheet in the body; and,
c) filling any space between the body and thermoformed sheet with heated liquid, the liquid being at least one of the same and a similar material.

Typically the method includes:
a) fitting the breathing assistance apparatus to the user;
b) checking the breathing assistance apparatus in use for at least one of:
  i) stability;
  ii) comfort; and,
  iii) breathing noises; and,
c) modifying the breathing assistance apparatus as required.

Typically the body defines:
a) at least one first opening for allowing airflow between lips of the user;
b) two second openings provided in the oral cavity to allow air flow into and out of a posterior region of the oral cavity; and,
c) two channels, each channel connecting a respective second opening to the at least one first opening and each channel passing at least one of at least partially along the buccal cavity and at least partially between the teeth to thereby provide an airway for the user, the airway at least partially bypassing the nasal passage and acting to replicate a healthy nasal passage and pharyngeal space.

A method for use in manufacturing an oral appliance, the method including:
a) determining a desired jaw position;
b) obtaining shape information indicative of a shape of the user's teeth with the user's jaws at least in the desired jaw position; and,
c) manufacturing the oral appliance at least in part using the shape information.

It will be appreciated that the broad forms of the invention and their respective features can be used independently and/or in conjunction and reference to these as separate forms of the invention is not intended to be limiting.

BRIEF DESCRIPTION OF THE DRAWINGS

An example of the present invention will now be described with reference to the accompanying drawings, in which:

FIG. 7A is a schematic front view of a spacer for use in determining a desired jaw position;

FIG. 7B is a schematic plan view of the spacer of FIG. 7A;

FIG. 7C is a schematic cross sectional view of the spacer of FIG. 7A along the lines A-A';

FIG. 7D is a second schematic cross sectional view of the spacer of FIG. 7A along the lines A-A', in use;

FIG. 8A is a schematic plan view of a second example of a spacer for use in determining a desired jaw position;

FIG. 8B is a schematic side view of the spacer of FIG. 8A in use;

DETAILED DESCRIPTION OF THE PREFERRED EMBODIMENTS

Figure 1A:
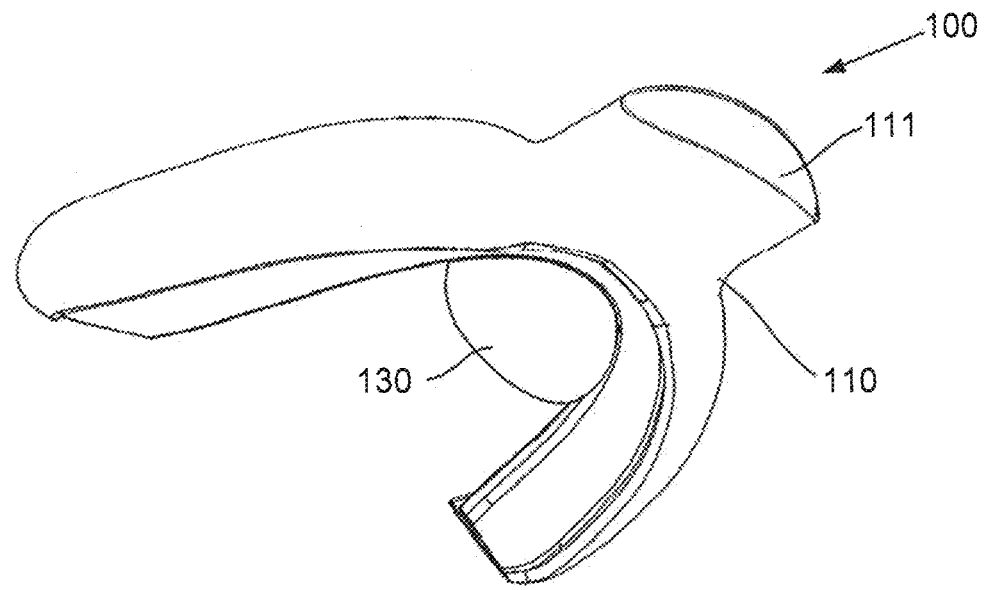
FIG. 1A is a schematic underside perspective view of a first example of apparatus for providing breathing assistance.
Figure 1B:
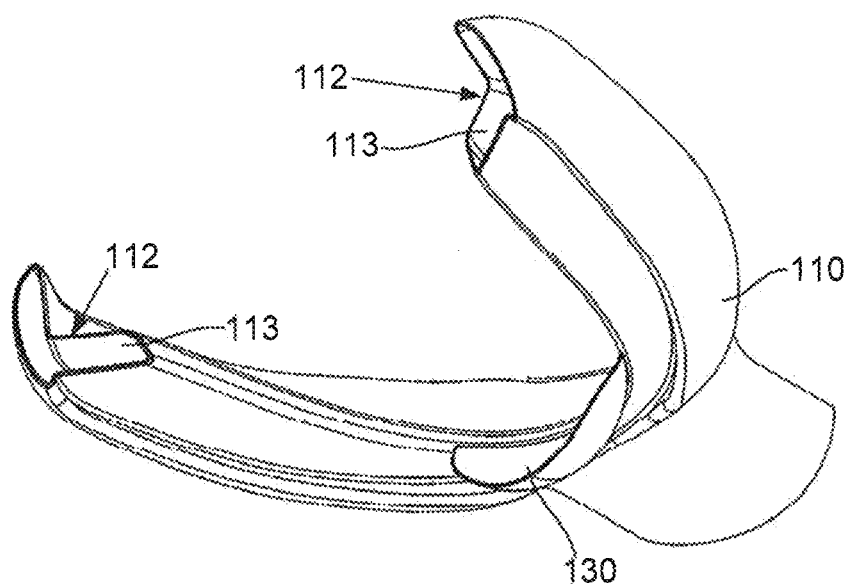
FIG. 1B is a second schematic underside perspective view of the apparatus of FIG. 1A.
Figure 1C:
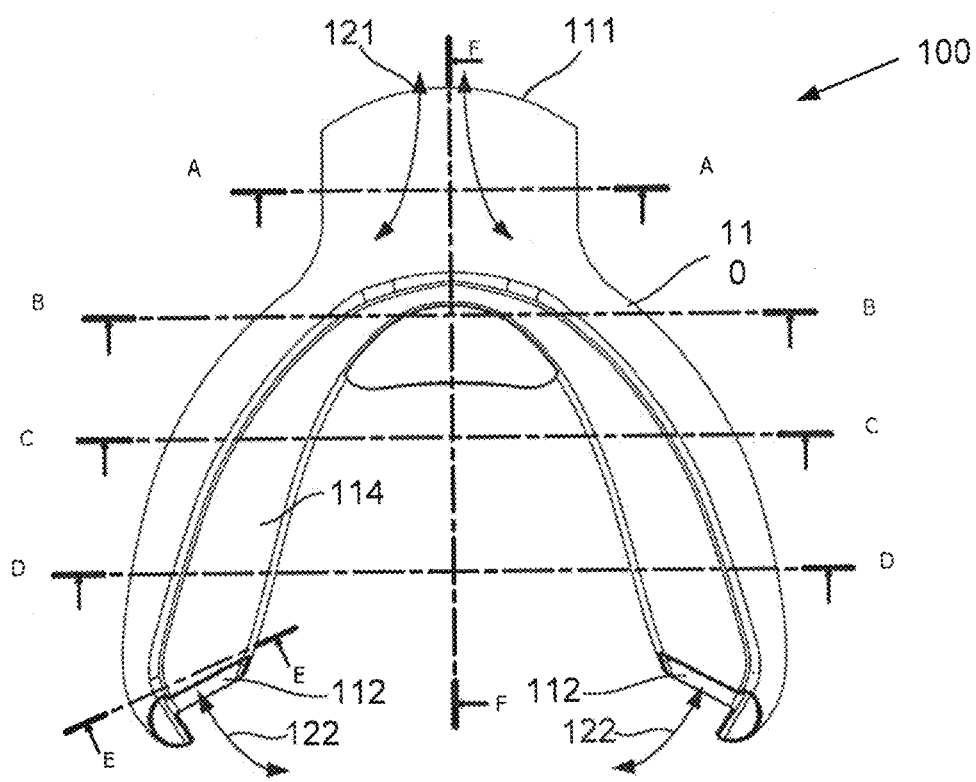
FIG. 1C is a schematic plan view of the apparatus of FIG. 1A.
Figure 1D:
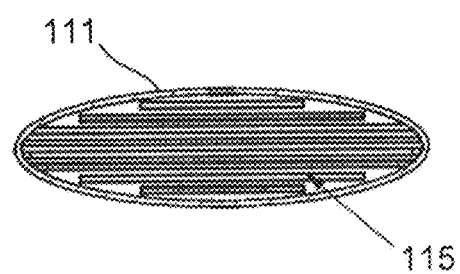
FIG. 1D is a schematic cross sectional view along the lines A-A of FIG. 1C.
Figure 1E:
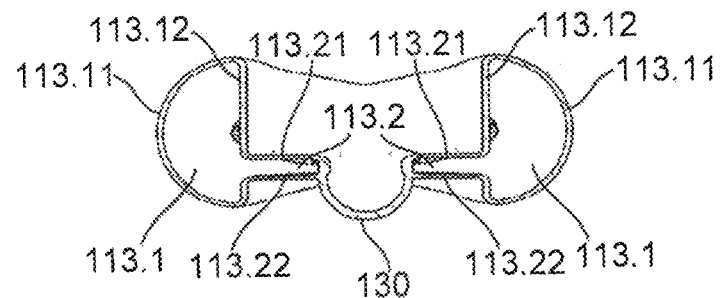
FIG. 1E is a schematic cross sectional view along the lines B-B of FIG. 1C.
Figure 1F:
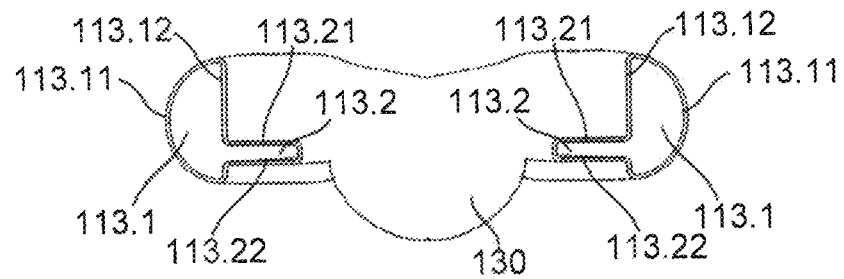
FIG. 1F is a schematic cross sectional view along the lines C-C of FIG. 1C.
Figure 1G:
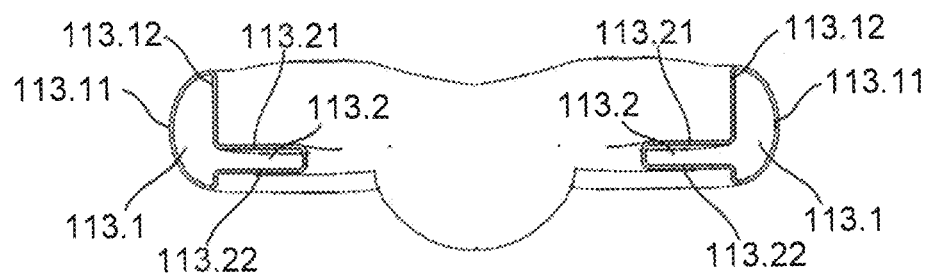
FIG. 1G is a schematic cross sectional view along the lines D-D of FIG. 1C.
Figure 1H:
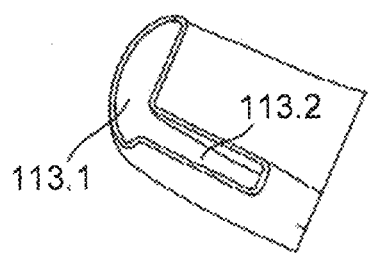
FIG. 1H is a schematic cross sectional view along the lines E-E of FIG. 1C.
Figure 1L:
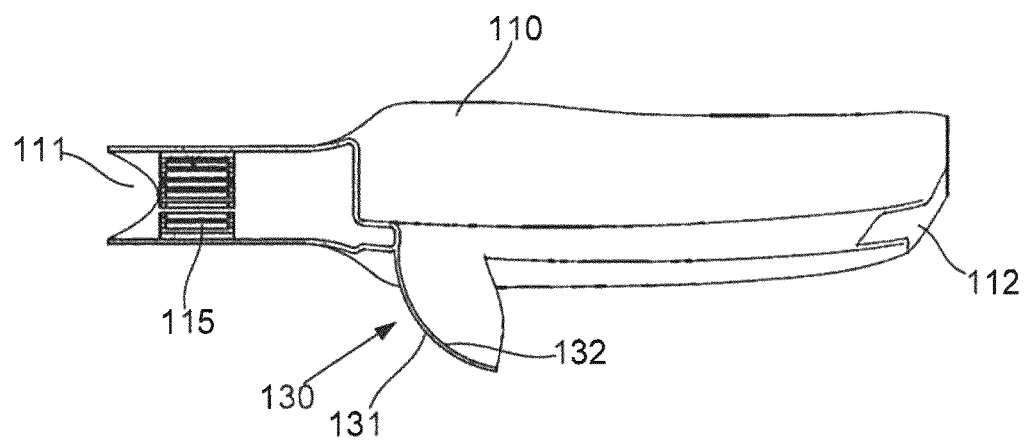
FIG. 1I is a schematic cross sectional view along the lines F-F of FIG. 1C.

An example of a breathing assist apparatus will now be described with reference to FIGS. 1A to 1I.

In this example, the apparatus 100 includes a body 110 for positioning within an oral cavity of a user. The body 110 includes at least one first opening 111 for allowing airflow between lips of the user and two second openings 112 provided in the oral cavity to allow air flow into and out of a posterior region of the oral cavity. Two channels 113 are provided, each channel connecting a respective second opening 112 to the first opening 111 and each channel 113 passing at least one of at least partially along the buccal cavity and at least partially between the teeth to thereby provide an airway for the user, the airway at least partially bypassing the nasal passage and acting to replicate a healthy nasal passage and pharyngeal space.

As a result of this arrangement, during inhalation, air can enter the apparatus 100 via the first opening 111, as shown by the arrows 121, pass along the channels 113, to the second openings 112. The second openings 112 are typically provided towards a posterior of the user's oral cavity, on a lingual side of the user's teeth, so that air is directed into the posterior of the oral cavity, as shown by the arrows 122. In one particular example, the channels 113 and second openings 112 are provided so that air flows through the user's hammular notch. During exhalation, airflow is reversed, as will be appreciated by persons skilled in the art.

Thus, the apparatus provides an oral appliance for providing breathing assistance. This can be used during sleep, for example for the treatment of both snoring and sleep apnea, and can also be used at other times, for example during exercising to assist with maintaining optimum airflow, in the treatment of respiratory conditions, such as emphysema, and to assist in supplying air, for example during surgery, CPR (Cardiopulmonary resuscitation), or the like. The device has a first opening 111, which can extend beyond the lips, or at least keep the lips apart, to allow airflow therethrough. Air passes through airways defined by the channels 113, on each side of the oral cavity, and is directed into a posterior region of the mouth through second openings 112, bypassing issues with tongue and lower jaw position. In more severe cases, the first opening 111 can be connected to an external device, such as a CPAP (Continuous Positive Airway Pressure) machine, air supply, or the like providing more comfort and increased patient compliance compared to a mask.

Providing air flow directly into a posterior portion of the user's oral cavity has a number of benefits. In particular, this avoids obstructions created by the nasal cavity, soft palate and tongue which can lead to snoring and apnoea events, and helps reduce the drying effects of air flow, which can in turn lead to user discomfort. This makes the apparatus comfortable to wear whilst ensuring an unobstructed air flow thereby preventing snoring and apnoea events. Thus, for example, nasal obstructions can be bypassed by air flow through the apparatus, thereby bypassing the nasal airway or adding to it in the case of a partial obstruction. Furthermore, air flowing below or on both sides of the soft palette helps prevent collapse of the soft palate, which can in turn lead to additional obstruction.

Additionally, during sports, the apparatus can act to provide protection to the user's teeth, for example by cushioning and/or absorbing impacts, whilst also providing for improved airflow.

In one example, the body is manufactured using additive manufacturing, such as a 3D printing process. This is particularly beneficial as it allows the channel arrangement 113 to be made, whilst minimising the thickness of the channel walls. This helps maximise the cross sectional area of the channels, thereby assisting airflow, whilst minimising overall device volume, thereby helping to maintain comfort. For example, the use of additive manufacturing allows a body having channel wall thicknesses of less than 0.5 mm and more typically approximately 0.3 mm or less, although it will be appreciated that other thicknesses can be accommodated if required. Thus, this significantly reduces the volume/bulk compared to an acrylic device made using standard processes, thereby maximising the available airway size, whilst also leading to more user comfort and improved compliance.

A number of further features will now be described.

In one example, for a device adapted to be used at rest, for example during sleeping or sitting, each channel has a cross sectional area of at least one of at least 10 mm$^2$, at least 20 mm$^2$, at least 30 mm$^2$, at least 40 mm$^2$ and at least 50 mm$^2$. Additionally, the at least one of the first opening and/or the second openings have a cross sectional area of at least one of at least 50 mm$^2$, at least 70 mm$^2$, at least 90 mm$^2$, at least 100 mm$^2$ and at least 110 mm$^2$. The dimensions selected will vary depending on a wide range of factors, including whether the device is required to provide a partial or complete airway, for example to bypass a partial or complete blockage. Additionally, this will depend on the intended use and the associated airflow requirements. Typically the dimensions of the channels 113 and/or openings 111, 112 are selected so that in conjunction with the user's existing airways, the total airway available corresponds to the cross sectional area of an airway in a healthy subject for both nasal and pharyngeal airways.

In any event, from the above it will be appreciated that the cross sectional areas used will depend on the preferred implementation and intended use, so for example, a smaller cross sectional area may be used for children, adolescents, or individuals with only partial obstructions. In contrast increased cross sectional areas may be used where a high flow rate is required, for example in the event that the device is to be used to provide breathing assistance during exercise.

The volume of air inhaled will vary depending on the level of activity. The following table is an indication of a male at rest, exercising and an elite sportsman. Clearly the volume of air required increases which is a result of both more breaths per minute and the volume of air in each breath.

|  | Male - at rest | Male exercising | Elite athlete exercising |
| --- | --- | --- | --- |
| Amount of air per minute - litres | 8 | 60 | 200 |
| Breaths per minute | 12 | 40 | 60 |
| Volume per breath - litres | 0.533 | 1.5 | 3.33 |
| Ratio compared to male at rest | 1 | 3 | 6 |

Consequently the size of the airway for the present invention will increase for a device that is to be used for aerobic activities. For general exercise this will be 2-3 times the area for use at rest and for elite sports 5-6 times the area.

As a result, for a device adapted to be used during exercise, each channel has a cross sectional area of at least one of at least 20 mm$^2$; at least 40 mm$^2$; at least 60 mm$^2$; at least 80 mm$^2$; at least 100 mm$^2$; at least 150 mm$^2$; at least 200 mm$^2$; at least 250 mm$^2$; and, at least 300 mm$^2$. Similarly, at least one of the first opening and the second openings have a cross sectional area of at least one of at least 100 mm$^2$; at least 140 mm$^2$; at least 180 mm$^2$; at least 200 mm$^2$; at least 220 mm$^2$; at least 330 mm$^2$; at least 440 mm$^2$; and at least 550 mm$^2$. It will of course be understood that different channel and opening dimensions could therefore be determined on a case by case basis depending on the intended usage.

The channels can have a wide variety of configurations and may be sized and shaped depending on the anatomy of the oral cavity of the user. This is typically done to maximise the available airway, whilst ensuring comfort for the user. In one example, this is achieved by measuring the oral cavity of the user, for example by taking dental impressions, a series of photos, or scans of the user's teeth and/or oral cavity and then customising the apparatus based on the measured size, as will be described in more detail below. In general however, the apparatus will have a number of common features irrespective of the user.

In one example, the channel includes two interconnected channel portions, including a first channel portion 113.1 extending through the buccal cavity, between the user's cheeks and teeth, and a second channel portion 113.2 in fluid communication with the first channel portion and extending between the user's maxillary and mandibular teeth. It will be appreciated that the channel portions are integrally formed and reference to them as separate portions is largely for the purpose of illustration. In any event, this arrangement maximises the cross sectional area of the channels 113, whilst maintaining comfort for the user, by distributing the airway between the user's teeth and cheeks and between the user's teeth. In particular, this avoids the second channel portion 113.2 between the teeth being too high, which would result in the mouth being held open too far, whilst also avoiding the first channel portions 113.1 causing the cheeks to bulge.

In one example, the first channel portion 113.1 has substantially semi-elliptical cross section and the second channel portion 113.2 has a substantially rectangular cross section, the second channel portion 113.2 extending laterally inwardly from the first channel portion 113.1. The use of a semi-elliptical cross section for the first channel portion, allows the curved outer surface 113.11 to lie against the inner surface of the user's cheek, avoiding sharp edges being in contact with the cheeks, and thereby ensuring comfort. The linear inner surface 113.12 can rest against the teeth, thereby maximising the volume of the first channel portion. The second channel portion 113.2 has a rectangular cross section, allowing the teeth to rest against the upper and lower faces 113.21, 113.22 of the second channel portion 113.2 in use.

In one example, the cross sectional area of the first and second channel portions vary between the first and second openings 111, 112. For example, in the arrangement of FIGS. 1A to 1I, the first channel portion progressively decreases from the first opening 111 to the second opening 112, whilst the cross sectional area of the second channel portion 113.2 progressively increases from the first opening 111 to the second opening 112. This allows the overall cross section of the channel 113 to be maintained, whilst having the channel portions 113.1, 113.2 conform as far as possible to the natural space available in the oral cavity. It will be appreciated that any variation can be used, depending for example on the configuration of the user's oral cavity.

Thus, the airways defined by the channels 113 have a cross section this is shaped to conform to a persons oral cavity, and in particular the available space between the maxillary and mandibular teeth, as well as between the teeth and the cheeks. In one example, the first opening 111 has an elliptical shape at the air entrance between the lips and also a semi-elliptical shape (vertical) along the gum line to the first molar on each side and then smoothly transition to an "L" shaped cross section from the first molar to the rear of the appliance, so that at least some of the airway is between the user's teeth in this area.

In one example, the first opening is removably mounted to the body. In this regard, this allows different styles of first opening to be used, for example to interface with an external device or the like, as well as allowing different sizes of first opening to be used to suit user requirements. This also allows for easy cleaning of the opening and/or replacement of filters, heat/moisture exchangers, valves or the like provided therein, as will be described in more detail below. The first opening can be made of any suitable material and could include plastic, metals, ceramics or the like and could also be made using different materials to the body.

In one example, the second openings are angled inwardly at between 10° and 50°, more typically between 20° and 40° and preferably about 30° to assist in airflow into and out of the oral cavity, and in particular to direct airflow towards the centre of the oral cavity. Additionally and/or alternatively, the second openings are positioned over the last or back tooth on each side of the top jaw.

As mentioned above, the body 110 is typically made using additive manufacturing, which in one example is used to create a body made of metal and in particular a titanium alloy and/or cobalt chromium alloy, although it will be appreciated that any suitable material may be used, including high strength polymers, plastics, VeroGlaze (MED620) dental material, or the like. The body can be coated with a medical grade polymer and in one example, a medical grade elastomer, such as silicone or polyurethane, epoxy or parylene, for improved comfort as well as ensuring biocompatability. In one example, the coating can include an Active Composite Guidance, which is a 3 dimensional composite resin with different shapes and sizes and which can be bonded to the body to ensure accurate positioning of the body with respect to the user's teeth. Coatings can be applied to the body using any suitable technique, such as dip coating, vapour coating, or spray coating the body, thereby ensuring all exposed surfaces, including internal surfaces of the channels, are coated. As part of this process, this can include applying primers to the body prior to coating, thereby ensuring the coating adheres to the body.

As an alternative, or in addition to coating, at least part of the body can be polished using at least one of mechanical and electrochemical polishing.

In one example, the apparatus includes a filter 120 for filtering air flowing through the apparatus. This can help remove particulates, pollen or other contaminants entrained in air flowing into the device, which can assist in reducing respiratory irritation, which can in turn exacerbate snoring and breathing difficulties. The filter 120 can be positioned anywhere within the body 110, but is typically provided within the first opening 111, thereby allowing this to be easily removed and replaced if required. The filter could be of any suitable form and could include a porous plastic or cloth based filter, and may include additional materials for added functionality. For example, the filter can also include activated carbon for filtering out pollution/bacteria.

Additionally, and/or alternatively a heat/moisture exchanger can be provided that controls the water and temperature content of the air being inhaled by exchanging heat and moisture with exhaled air. Examples of such exchangers can be found for example in U.S. Pat. No. 5,433,192, and these will not therefore be described in any further detail.

Additionally or alternatively, the apparatus can include a valve (not shown) for regulating air flow through the apparatus. In one example, this can be used to resist outflow of air from the second openings to the first opening. This can assist in regulating breathing and in particular allow for rapid inhalation, whilst ensuring slower exhalation, thereby optimising gas exchange within the lungs, for example to minimise the chances of hyperventilation. The valve can be of any suitable form, such as a ball valve, umbrella valve, or the like, and can be adjustable or titratable to ensure that the level of flow control is appropriate to the user.

The body can include a lingual flange 130 for engaging mandibular teeth to thereby maintain mandibular position. In this regard, the lingual flange 130 includes a first face 131, which in use, engages the user's mandibular incisors, thereby controlling the relative positions of the maxillary and mandibular jaws. In this regard, it is known that temporomandibular joint disorder (TMD) arises when the upper and lower jaws are misaligned. This may be naturally occurring or can result from injury, or the like. Regardless, such jaw misalignment tends to contribute to airway obstructions by changing the shape of the upper airway, and moving the tongue towards the posterior of the oral cavity, which can in turn exacerbate issues associated with OSA and snoring. Accordingly, providing the lingual flange 300 at an appropriate location allows the jaws of the user to be aligned thereby reducing the effects of TMD, and hence further reducing the likelihood of snoring and OSA. As will be described in more detail below, the apparatus can further include an insert that can be adapted to cover the first face of the lingual flange, with different thicknesses of the insert being provided to allow for thereby adjustment of mandible position in defined increments.

In addition, a second side 132 of the lingual flange can be provided to define a pocket for receiving the user's tongue. In this regard, the second side 132 is of a concave shape, so that when the tongue abuts against the lingual flange 132 a suction effect is created, thereby helping to retain the user's tongue towards the anterior of the oral cavity, which in turn helps further reduce airway obstruction caused by the position of the user's tongue.

Thus, in the current example, the lingual flange 130 is rounded and faces downwards and rearwards at an appropriate angle, such as 45° to suit the shape of the lingual region under the tongue for the bottom side as well as the top to comfortably allow the tongue to be positioned.

In one example, the lingual flange is movably mounted to the body to thereby allow adjustment of a user's mandibular position. Whilst this can be achieved in any suitable manner, in one example, the lingual flange 130 includes a flange recess for receiving a flange mounting projecting from a lower surface of the body 110. A screw is provided extending through the lingual flange and the flange mounting, so that as the screw is rotated the relative position of the flange mounting within the flange recess is adjusted, thereby progressively moving the flange. It will therefore be appreciated that movably mounting the flange 130 to the body 110, allows the relative degree of mandibular advancement to be adjusted to thereby provide an optimum outcome for the user.

Figure 2:
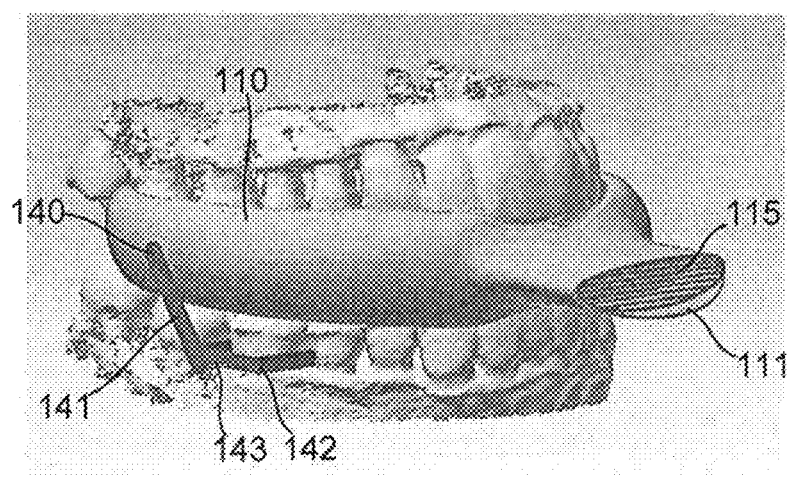
FIG. 2 is a schematic side view of the apparatus of FIG. 1A when connected to a mandibular repositioning device.
Figure 3A:
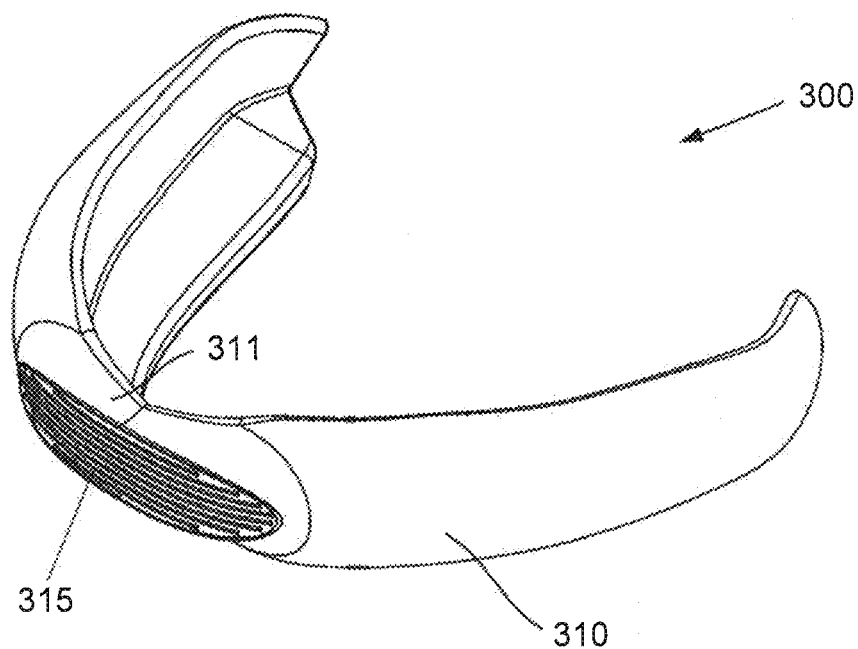
FIG. 3A is a schematic underside perspective view of a second example of apparatus for providing breathing assistance.
Figure 3B:
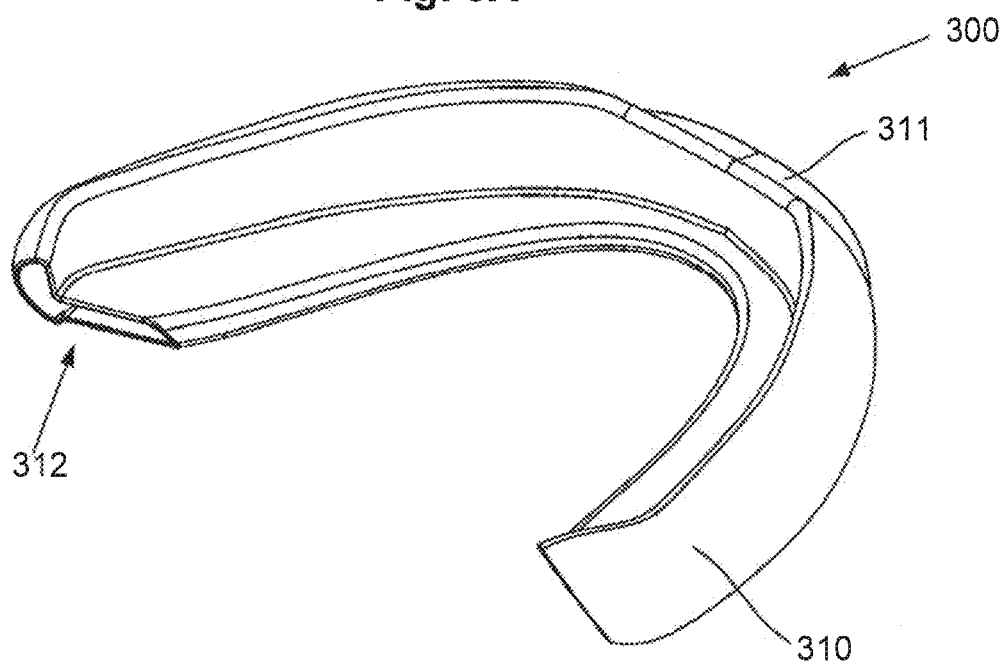
FIG. 3B is a second schematic underside perspective view of the apparatus of FIG. 3A.
Figure 3C:
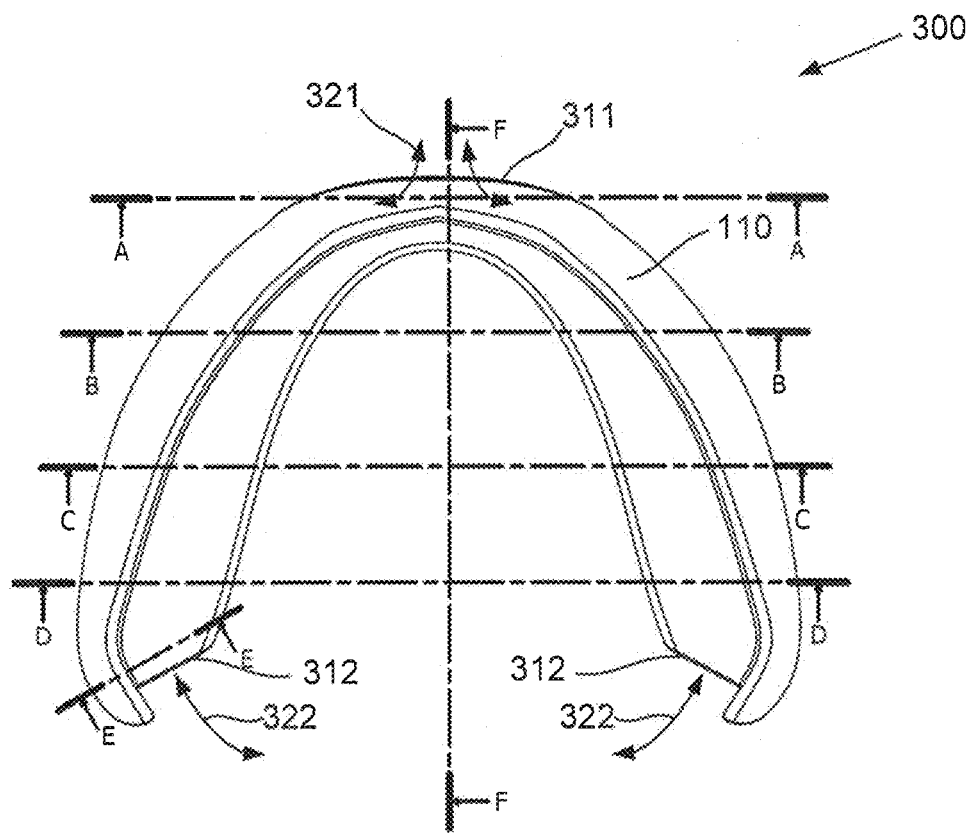
FIG. 3C is a schematic plan view of the apparatus of FIG. 3A.
Figure 3D:
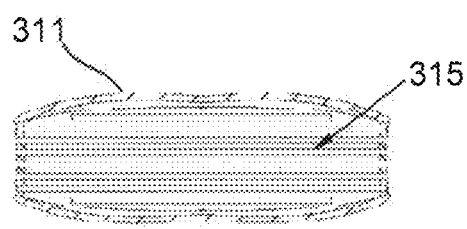
FIG. 3D is a schematic cross sectional view along the lines A-A of FIG. 3C.
Figure 3E:
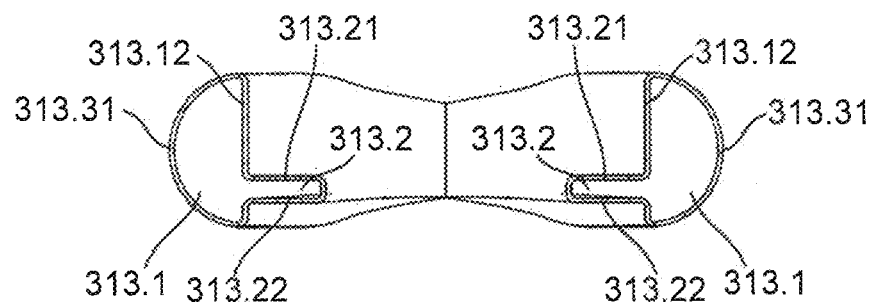
FIG. 3E is a schematic cross sectional view along the lines B-B of FIG. 3C.
Figure 3F:
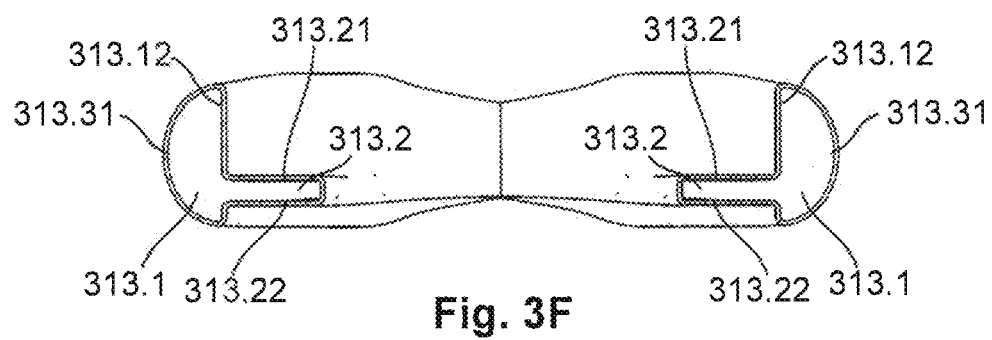
FIG. 3F is a schematic cross sectional view along the lines C-C of FIG. 3C.
Figure 3G:
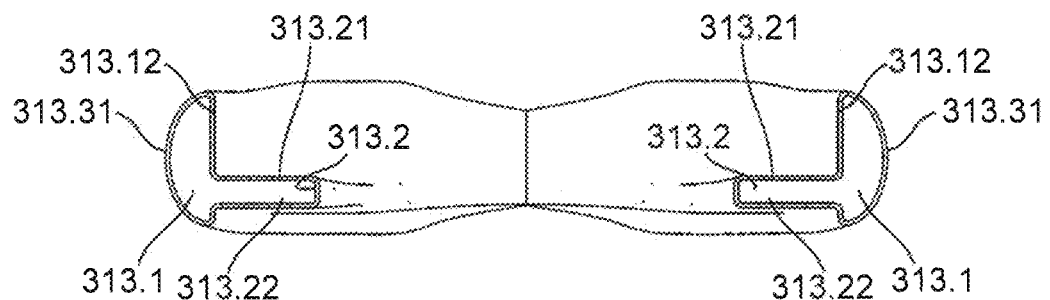
FIG. 3G is a schematic cross sectional view along the lines D-D of FIG. 3C.
Figure 3H:
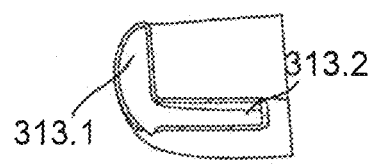
FIG. 3H is a schematic cross sectional view along the lines E-E of FIG. 3C.
Figure 3I:
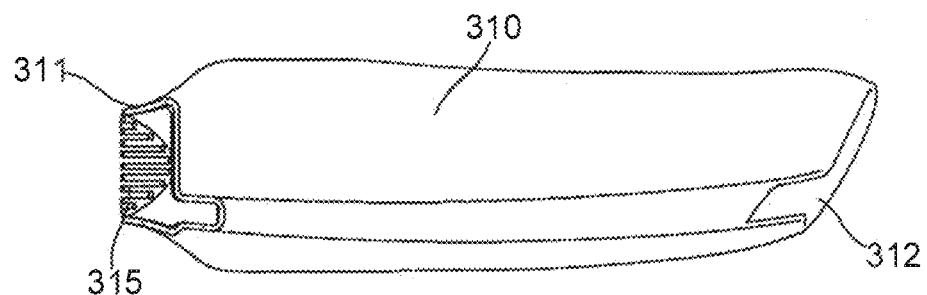
FIG. 3I is a schematic cross sectional view along the lines F-F of FIG. 3C.

As shown in FIG. 2, additionally and/or alternatively the apparatus can include a connector 140 for coupling the body to a mandibular repositioning device, for example including arms 141 connected to a retainer 142, via an optional hinge 143 for engaging the teeth. Thus, in one example, the connector 140 couples to adjustable arms, formed from either variable length or removable/replaceable arms of different lengths, can be used to connect the body 110 to particular teeth, such as the first mandibular molars, thereby allowing for 1 mm adjustments for bringing the mandible forward.

A second example apparatus suitable for use in sporting applications or the like is shown in FIGS. 3A to 3I. In this example, similar reference numbers increased by 200 are used to refer to similar features. It will therefore be appreciated that this is largely a different shape of opening 111, which no longer projects beyond the user's lips. This can assist in sporting scenarios by reducing the likelihood of impact with the apparatus, whilst still assisting in urging the user's lips apart to ensure adequate airflow. In this example, the apparatus also does not include a lingual flange as the presence of this could lead to damage to teeth in the event that an impact occurs. The device can also include mesh extending from the body, the mesh extending past the tooth gum interface and to the sulcus of the user on at least one of a lingual and labial side to thereby provide protection to teeth of the user in use. It will be appreciated that this can assist in absorbing impacts thereby protecting the user's teeth, whilst also ensuring an airway is maintained.

In any event, whilst this has been described as being useful in sporting applications, it will be appreciated that this is not necessary and that in any event this highlights that a range of different configurations can be provided.

Figure 4A:
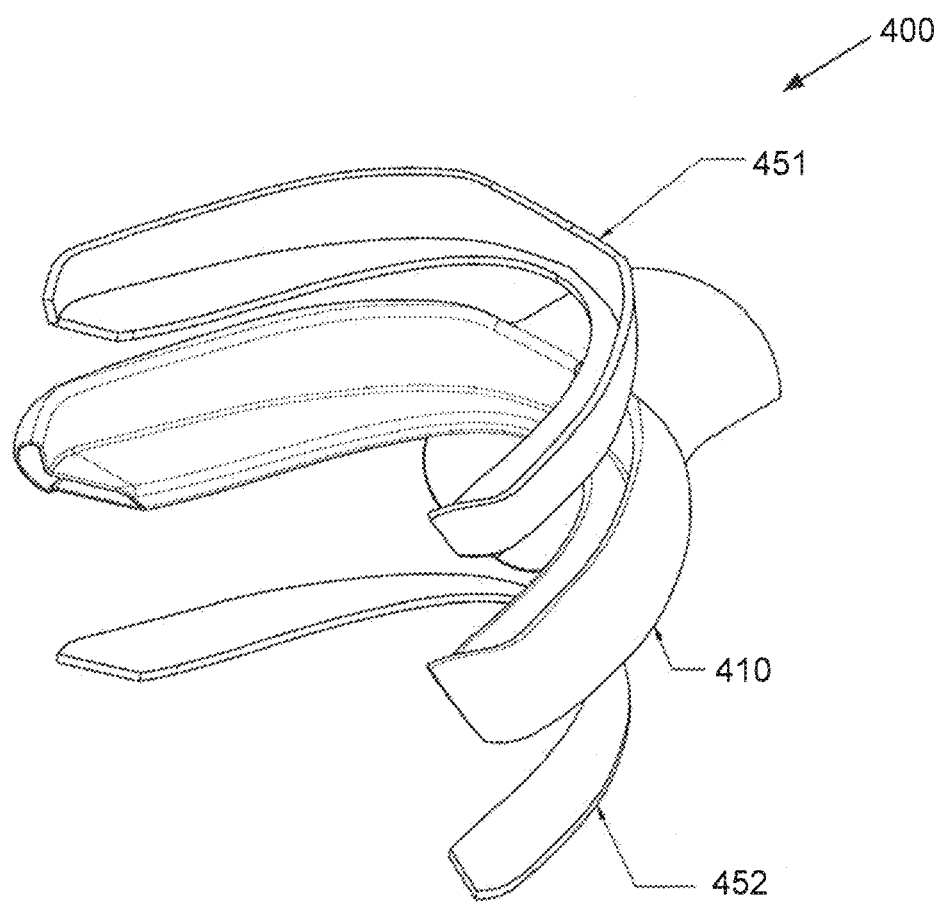
FIG. 4A is a schematic topside perspective view of a third example of apparatus for providing breathing assistance.
Figure 4B:
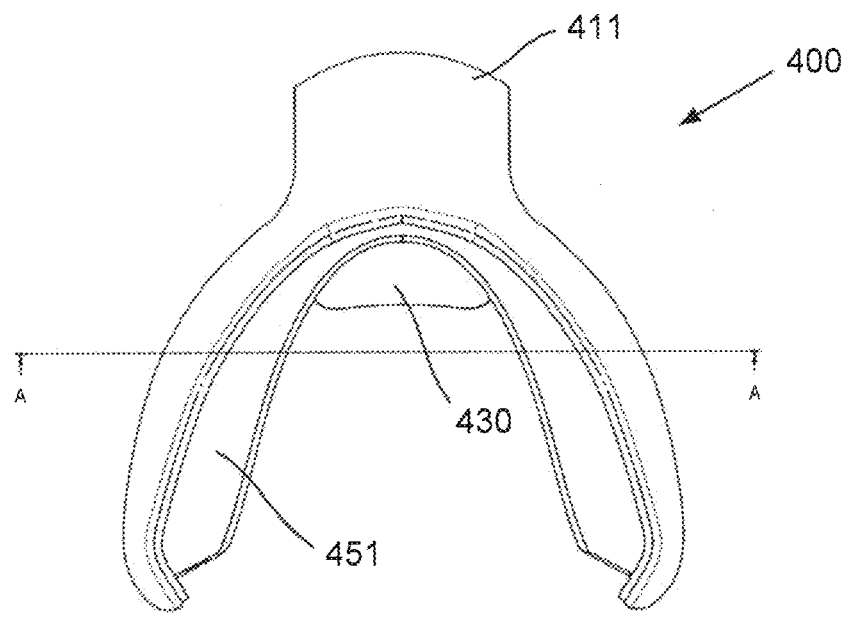
FIG. 4B is a schematic plan view of the apparatus of FIG. 4A.
Figure 4C:
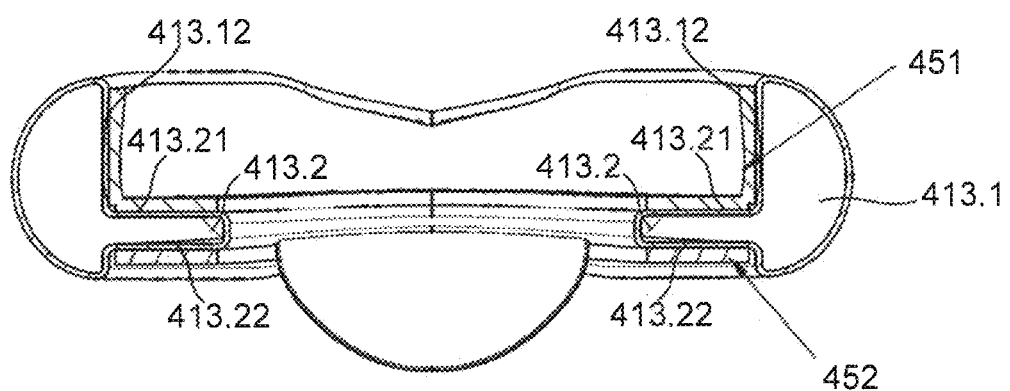
FIG. 4C is a schematic cross sectional view along the line A-A of FIG. 4B.

A second example apparatus is shown in FIGS. 4A to 4C. In this example, similar reference numbers increased by 300 are used to refer to similar features.

In this example, the apparatus 400 includes at least one, and more typically two inserts 451, 452, the inserts being positioned between the user's teeth and the body 410 in use. The inserts generally have an arcuate shape and "L"-shaped cross section so that they conform to the shape of the channels. In particular, an upper insert 451 is adapted to abut against the and the upper face 413.21 of the second channel portion 413.2, whilst a lower insert 452 abuts against the linear inner surface 413.12 of the first channel portion 413.1 and the lower face 413.22 of the second channel portion 413.2.

The insert(s) are typically formed from acrylic, polyvinylsiloxane, polyurethane or ethylvinylacetate, another suitable polymer or the like, and are optionally customised for a user's teeth, thereby maximising comfort of the device in use. The inserts can be removable or replaceable, allowing a plurality of different inserts to be provided with each insert being adapted to provide a different positioning of at least one of the body and the user's teeth.

In one particular example, the apparatus includes an insert having a lingual flange layer extending over at least part of the lingual flange and wherein a thickness of the lingual flange layer is used to adjust the user's mandibular position. Thus, the apparatus can include multiple inserts for each user, and wherein each insert has a different lingual flange layer thickness for adjusting the user's mandibular position in known increments.

The inserts can also be adapted to provide impact protection for example for use in sports applications.

When manufacturing the above described apparatus, this typically involves creating a custom apparatus for each user. In order to achieve this, the method typically includes obtaining shape information indicative of a shape of the user's oral cavity and then manufacturing the breathing assist apparatus using the shape information.

The shape information can include dimensions of the oral cavity of the user and can be derived from a scan, such as a CT scan of the user's oral cavity, or alternatively can be obtained from dental impressions, 3D models, 3D scans of the user's teeth, cone beam imaging, moulds, digital impressions of an intra-oral scan, or the like. Alternatively, the dimensions could be obtained from a series of photos of the patient's mouth or impressions taken with a smart phone or the like.

As part of this process, the method can involve selecting one of a number of standard bodies in accordance with the shape information and using the shape information, at least one of modifying the selected standard body and creating at least one insert. Thus, a range of standard template bodies can be provided, with these being modified as required in order to prepare a custom body for each user. Thus, for example, a range of template devices, such as 6 to 10 designs can suit 80-90% of patients which can then be selected and then individually customised by the dentist or dental laboratory for each patient.

The modification/customisation can be performed by adding custom inserts and additionally or alternatively custom manufacturing or finishing of the body. Custom manufacturing can include obtaining template data representing a body design, modifying the body design using the information derived from the shape information, generating modified template data using the modified body design and then manufacturing the body using the modified template data. In one particular information, the modified template data is in the form of a print file for use in an additive manufacturing machine. Thus, for example, this process can be used to generate a custom STL (STereoLithography) print file, thereby allowing a body 110 to be custom printed for each individual. Thus, for example, a series of photos could be loaded into a software program to derive a 3D image, which is then used to generate an STL file. However, alternatively, customisation can be a post manufacture process of shaping using convention techniques.

As part of the above manufacturing process, additional components, such as the mandibular advancement mechanisms or inserts can be included in the STL file and hence "printed" into the device.

In one particular example, the manufacturing process uses additive manufacturing of titanium using an STL file which is a merging of the device design features adapted to suit scans of the patients mouth or scans of an impression of their teeth, although alternatively a limited number of standard shapes could be used, with these being customised by hand or machining using standard techniques, or through the use of separate additional custom inserts.

In one example, when the body 110 is produced it is cleaned and then coated with a suitable polymer material such as a medical grade elastomer eg: silicone or polyurethane or polymers such as epoxy. This can be achieved using a dipping or spray process either by hand into a container of the solution or using dedicated equipment such as those available from DipTech Systems Inc in the USA. The use of dip or spray coating solutions allow for the coating of the inner areas of the airways. Primers may be used to optimise adhesion or the natural surface roughness of the device does provide mechanical attachment. Examples of the coatings include but are not limited to: MED16-6606 RTV Silicone Dispersion from Nusil Technology 1050 Cindy Lane, Carpinteria, CA 93013; Baymedix SD for seamless polyurethane films from Bayer MaterialScience AG 51368 Leverkusen Germany, 301-2 and 302-3M for epoxy or cyanoacrylate coatings from Epoxy Technology, Inc. 14 Fortune Dr. Billerica, MA 01821

In another example, when the body 110 is produced it is cleaned and then coated with a suitable polymer material such as a medical grade polymer from the vapour form such as parylene. Such equipment and material can be supplied by Specialty Coating Systems Ontario, California USA.

In another example, when the body 110 is produced it is polished using mechanical and/or electrochemical means. This may be with abrasive bits and polishing pads using hand or bench tools. It may also be achieved using specialised abrasive and electrochemical treatment from companies such as from Best in Class (BinC) Industries in St Priest France As previously described, a mandibular advancement arrangement can be incorporated. In one example, this is in the form of a fixed lingual flange 130 printed as part of the body 110. Alternatively, if an adjustable mechanism is required, the lingual flange 130 is provided as a separate component which is positioned on a track with a screw adjustment. Alternatively, arms (metal or plastic) can be attached to the upper airway appliance and then to the occlusal region of the mandibular teeth. These can be easily fitted by the patient using screws or other mechanical attachment methods In any event, the above described apparatus provides a dental insert that provides an airway running from between the lips into the buccal sulcus and/or between the teeth then into the area over or behind the wisdom teeth, through the hamular notch and then opening into a region near or just off the soft palate. This provides an alternative airway, helping mitigate the impact of partial or total obstructions either in the nasal passages, soft palate or created by the tongue, thereby reducing the impact of such obstructions, and hence preventing snoring and OSA.

The provision of a lingual flange can be used to move a user's mandible forward, helping to prevent obstruction by the tongue, thereby maintaining a clear glossopharyngeal airway, with the degree of advancement being controlled depending on severity of symptoms. For example, this can be to the extremity of the neuromuscular zone of tolerance or beyond if necessary to clear tongue obstruction. The concave inner surface of the tongue flange, together with an optional tongue recess, can also act as a suction cup to hold the tongue forward.

In addition to this, the apparatus can assist in maintaining alignment of the upper and lower jaws can reduce the impact of TMD.

The apparatus may also include a screw inserted into the lingual flange allowing the apparatus to be titratable for use with PSG (Polysomnograph) and EMG (Electromyograph).

It will be appreciated from the above described examples, that the use of an airway running from the lips into the buccal sulcus and/or between the teeth then into the area over or behind the rear teeth or wisdom teeth, through the hamular notch and then opening into a region near or just off the soft palate could be implemented as part of existing insert that includes a body insertable into the oral cavity. Accordingly, the above described examples are for the purpose of illustration only and are not intended to be limiting.

Accordingly, it will be appreciated that the above device can treat individuals with sleep apnea (especially more severe cases) but typically is more comfortable than and hence will have greater compliance rates compared to a mask. In this regard, it has been shown that there is 30-50% of CPAP users are non-compliant/non-users within 2 years of starting their treatment and further recent studies have shown that mouth breathing is an indication for non compliance.

The apparatus can assist in significantly improving sleep as shown by both sleep studies and general home use (quality of sleep and daytime function) with or without a CPAP. The apparatus overcomes the issues of dry mouth and ideally reduces the number of cases of excessive salivation with initial use. The device is more comfortable to wear leading to lower side effects such as teeth rubbing, teeth movement, jaw misalignment, or perceived "mouth noise" with movement. Additionally, the apparatus does not cause any damage to dentine layer of the teeth, has lower cost to manufacture and therefore when and if required, can be profitable if current selling prices are reduced, and complies with regulatory requirements.

However, whilst the above description has focussed on applications of sleep apnoea and snoring, use of the apparatus is not so limited and can apply in any scenario where breathing assistance is required.

For example, the apparatus can be used in sports applications to deliver more air into athletes lungs and allow them to breathe more easily during training/exercise. In these cases the airways may be larger but the fundamental design is the same. The apparatus can be used in general well being where people have a blocked nose from a cold or allergies, as well as to assist in delivery of other therapy such as steam to help alleviate congestion and airway irritation, for example, from asthma. In this regard, it will be appreciated that the use of an in-built filter can help reduce irritation from pollutants, whilst the use of a control valve can assist in regulating breathing, thereby improving breathing efficiency, and mitigating the effects of breathing difficulties. The valve can also control the rate of air when breathing in and then slow down for breathing out to help balance the oxygen and $CO_2$ exchange in the lungs and reduce the chances of hyperventilation or lactic acid build up in athletes. The device can also be used for treating pulmonary or respiratory disorders such as COPD (Chronic Obstructive Pulmonary Disease) or emphysema, to replace the use of a mask or be in addition to other airway devices for example during administration of oxygen, air, anaesthetic, CPR or the like, as well as for other day to day activities.

It will also be appreciated from the above that the apparatus could form part of an orthodontic or dental appliance, in which case the airway could be integrated into a body also having other functionality.

It will also be appreciated that the inserts could be made to have a gap or space between the teeth and the walls of the insert which would allow teeth whitening gel to be used while wearing the device.

Figure 5:
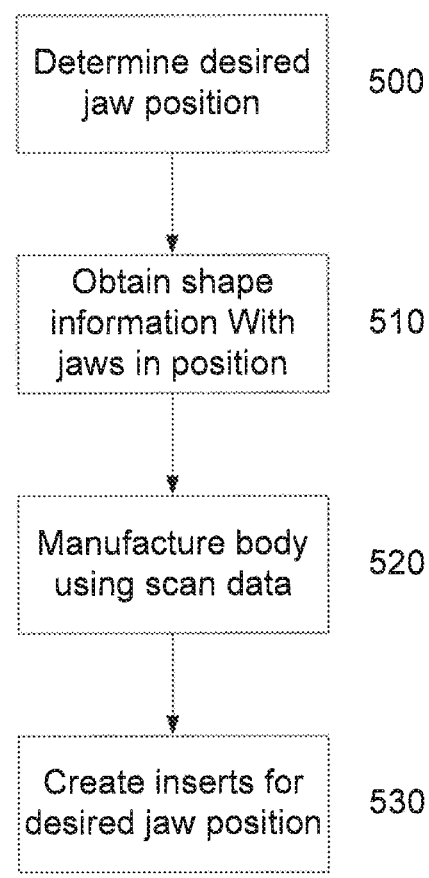
FIG. 5 is a flow chart of an example of a method for manufacturing a breathing assistance apparatus.
Figure 6:
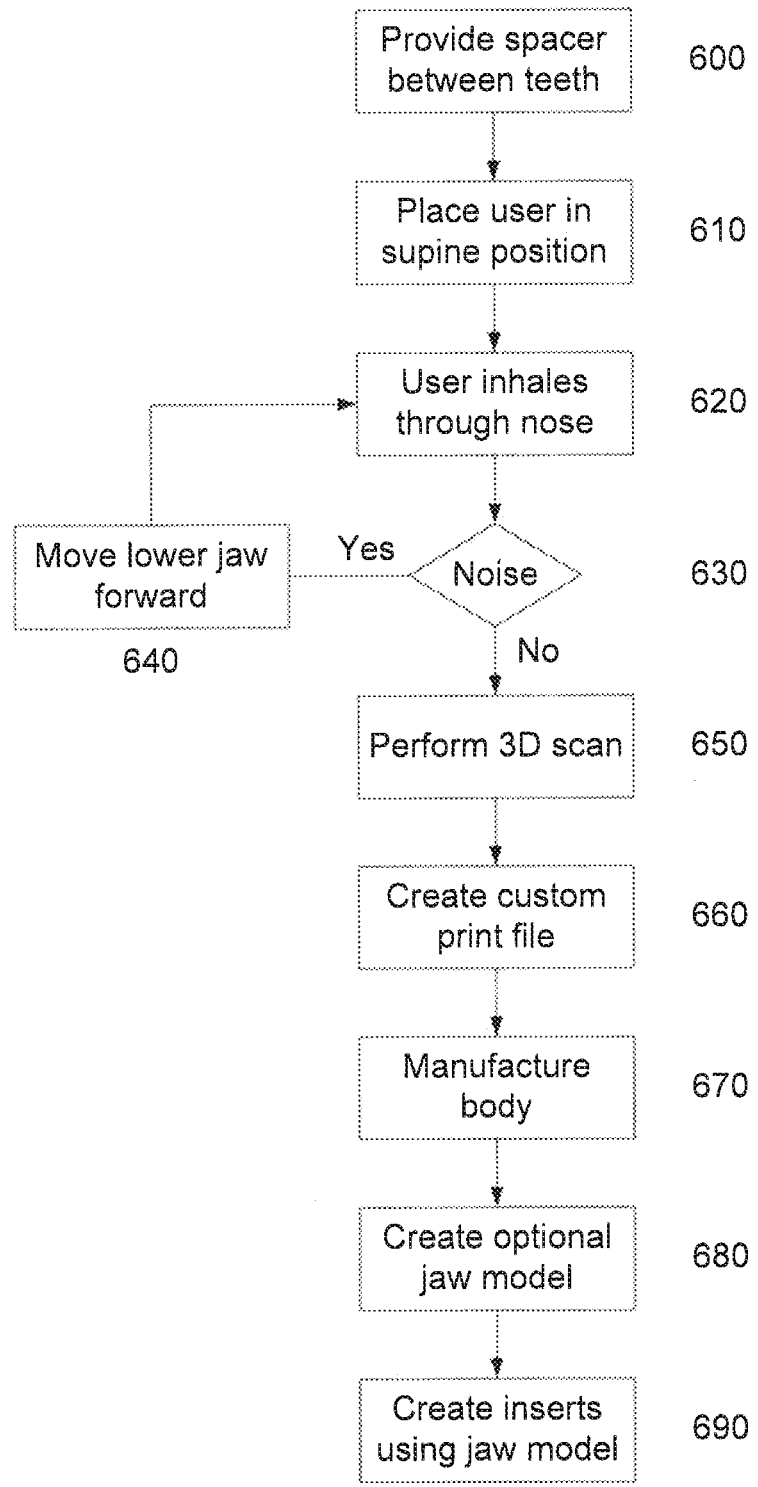
FIG. 6 is a flow chart of a further example of a method for manufacturing a breathing appliance.

An example of a method for use in manufacturing a breathing assistance apparatus for a user, and in particular for manufacturing a custom breathing assistance apparatus will now be described with reference to FIG. 5.

In this example, at step 500, the method includes determining a desired jaw position. In this regard, a desired jaw position is taken to be the jaw position that will be assumed by the user when the breathing assistance apparatus is being worn and in particular a jaw position that is comfortable and optimises airflow for the user, thereby minimising snoring or other undesirable breathing events.

The desired jaw position will typically vary for each user depending on a range of different factors, such as occlusal vertical dimension, tongue size, inter-arch relationship, tooth alignment, jaw joint function, soft tissue condition, lymphatic tissue, periodontal status, Maxillary Bone architecture, arch form, palatal vault. Accordingly, it is typical to determine a desired jaw position that is likely to clear glossopharyngeal obstruction while maintaining comfort.

Thus, the desired jaw position typically allows for the maxillary and mandibular teeth of the user to be spaced apart to a sufficient degree to accommodate the breathing assistance apparatus and optionally with the lower jaw advanced to move the tongue forward within the oral cavity.

Following this, at step 510 shape information indicative of a shape of the user's teeth with the user's jaws in the desired jaw position is obtained. This can be achieved in any appropriate manner as previously described, and this could include obtaining a bite impression, which is subsequently scanned, but more typically includes scanning the user's teeth and jaws, while the jaws are in the desired jaw position, for example using Cone Beam Computed Tomography (CBCT), CT scans, digital impressions of an intra-oral scan, or the like. Alternatively, this could be achieved using a 3-D imaging technique or the like as will be described in more detail below. Thus the desired jaw position determined at step 500 is typically recorded, for example using a bite registration material, positioning spacer, or the like, with this being used during a subsequent scanning process allowing the shape information to be obtained whilst the jaws are in the desired jaw position.

At step 520, a body of a breathing assistance apparatus is manufactured at least in part using the shape information. This could include creating a custom designed body, and typically includes modifying an STL print file or the like, of a standard template body, in accordance with the shape information.

At step 530, at least one insert is manufactured for the desired jaw position of the user, allowing the insert to be positioned at least partially between the user's teeth and the body in use, to thereby make the apparatus more comfortable to wear. This could be achieved in any suitable manner, typically involves curing a resin once it has been moulded into a desired shape.

Accordingly, the above described process involves placing the user's jaws into desired jaw positions before shape information is determined. The shape information can then be used to manufacture the body of a breathing assistance apparatus, or other oral implant, ensuring that this is appropriately configured for the user, and in particular to ensure the user's jaws are held in the desired jaw position, so that breathing is optimised.

A second example of a method for use in manufacturing a breathing assistance apparatus for a user will now be described with reference to FIG. 5.

In this example, at step 600 the desired jaw position is determined at least in part by providing a spacer between the user's teeth. The nature of the spacer will vary depending on the preferred implementation and could include the user's tongue, a laminar member including markings indicative of a relative jaw position or a folded piece of paper, or other suitable radiolucent spacer. The spacer is typically designed to ensure the user's maxillary and mandibular teeth are spaced apart by between 3 mm and 5 mm and more typically between 3.5 mm and 4.5 mm. However, it will be appreciated that the spacing is user dependent, and alternative spacings could be used as appropriate. The spacer may also be designed to induce advancement of the lower jaw, and this could be achieved in any suitable manner, such as by using markings to guide the user, indentations on the spacer, or by forming the spacer from relatively positionable bodies. Some specific example spacers will now be described. In another example, the spacer includes top and bottom arch trays that move relative to each other.

A first example spacer is shown in FIGS. 7A to 7C. In this example, the spacer 700 includes first and second spacer bodies 710, 720, each of which is curved and includes a recess 711, 721 for receiving at least some of the user's maxillary and mandibular teeth $T_{max}$, $T_{min}$, respectively. Each spacer body 710, 720 includes respective body serrations 712, 722, which cooperate to allow the relative position of the bodies 710, 720 to be controlled, thereby allowing the relative degree of advancement of the lower jaw to be adjusted.

Figure 8C:
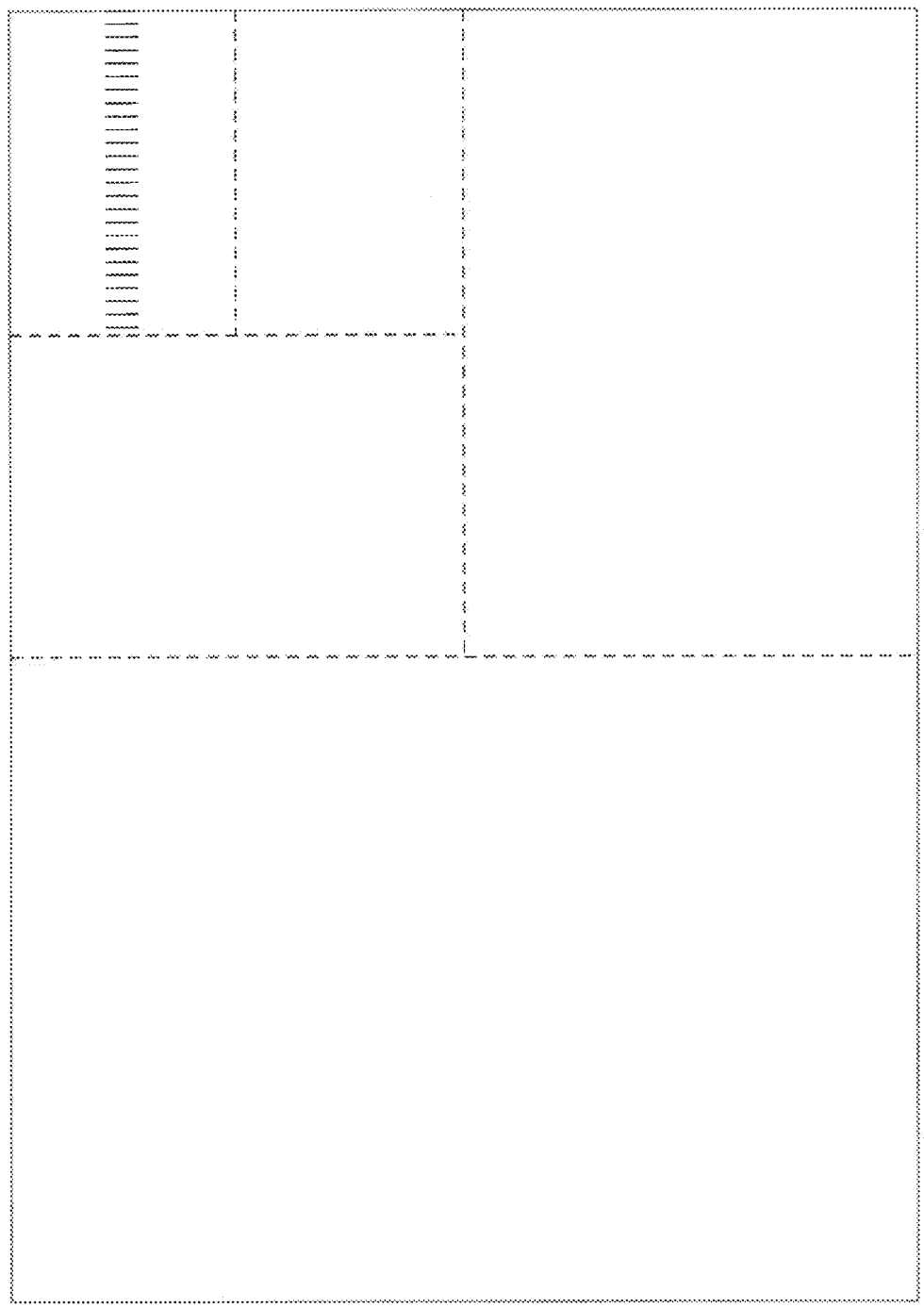
FIG. 8C is a schematic plan view of an example of a sheet for making the spacer of FIG. 8A; and, FIG. 9 is a flow chart of an example of the process for providing breathing assistance apparatus to a user.

A second example spacer is shown in FIGS. 8A and 8B. In this example, the spacer 800 includes a planar body 810 having graduations marked on upper and lower surfaces. In use, a user can provide their thumb T and forefinger F on desired markings and then align their teeth with the thumb and forefinger as shown to provide the jaws at desired jaw positions.

The second spacer could be provided in the form of a piece of card or plastic having a desired thickness. In another example, this can be achieved by folding a sheet of A4 paper along the dotted fold lines shown, with this resulting in a spacer having the required thickness.

However it should be noted that when the user places their tongue between the maxillary and mandibular teeth, this generally results in the correct spacing of the jaws and suitable advancement of lower jaw and so as a first approximation, this is often the preferred method for determining the desired jaw position.

At step 610, once the user's jaws are provided in the desired jaw position by the spacer positioned between the user's teeth, the user is placed in a supine position before the user breathes at step 620. In particular, the user is asked to breathe deeply through their nose, with the breathing action being assessed at step 630 to determine whether there is any undue breathing noise indicative of UARS (Upper Airway Resistance Syndrome) or snoring. If so, the process includes advancing the lower jaw at step 640, with the process of breathing and assessing breathing noise being repeated. This process continues either until most breathing noise is eliminated, or until the jaw advancement is no longer comfortable, at which point the process is halted and the current position is used as the desired jaw position, with this being recorded using the spacer, for example, based on the relative position of the bodies 710, 720, the position of the user's tongue, or markings on the spacer.

Once the desired jaw position has been determined, shape information is determined at step 650, in this example by scanning the user's teeth and optionally jaws using 3D scanning, such as CBCT scanning, with the jaws held in the desired jaw position using the relevant spacer. In this regard, the spacer is radiolucent, allowing this to be used during the scanning process. Additionally, scanning is typically performed with the jaws in opened and closed positions.

Alternatively, scanning can be performed using one or more intraoral cameras that are used to take multiple photos of the mandible (lower arch) and maxilla (top arch) at a macro and micro level. Various dental tools including bite blocks retractors and mirrors can be used to facilitate this process, for example to provide unrestricted access to the oral cavity and hence the teeth.

With the spacer in position (and mandible positioned appropriately relative to the maxilla) this process is repeated to take multiple photos of several segments of the teeth or the full teeth set with the retractors in place to define and record the position of the maxilla relative to the mandible for the purpose of fabrication of an appliance. The spacer can then be eliminated from the resulting image using image processing techniques, before the images are analysed to identify key indicator points.

Alternatively, dental impressions with the required bite relationship can be directly scanned using suitable computed tomography (CT) equipment, such as a dental imaging system from Carestream Health in Rochester New York USA Following this, and using information regarding the location of the key indicator points, if required the 2D dicom images (in the case of CT) are converted into a 3D model and/or STL file of the full teeth set in the required relationship to allow for the fabrication of an appliance using the steps described below. It will be appreciated that this image manipulation and conversion to a 3D model can be performed using existing image processing techniques and these will not therefore be described in further detail.

At step 660, the shape information, in the form of scanning data is provided to a manufacturing facility, allowing a manufacturer to prepare a custom print file, such as an STL file. This is typically achieved by modifying a print file in accordance with the shape information, with this being used to manufacture the body of the breathing assistance apparatus at step 670.

At step 680, a physical jaw model can be created by using the shape information to create an STL file, which is then used to additive manufacture a model of the user's jaws. The model is typically a plastic model created using 3-D printing or the like.

At step 690, one or more inserts are then created by applying a resin to the body, moulding the resin based on user's teeth with jaws in the desired jaw position and then curing the moulded resin. The nature of the resin used will vary depending on the preferred approach and this could include a chemical or thermosetting resin, such as a silicone resin, as outlined previously. This process can either be performed by applying the resin and having the user place the body in their mouth and bite into the resin, or alternatively can be performed using the model jaws, for example by positioning the body within the jaw models and then injecting a resin so that it surrounds the teeth of the model.

The use of model jaws to create the inserts is particularly advantageous as it allows the breathing assistance apparatus to be manufactured without requiring the user to be physically present, other than for the scanning step. Accordingly, this process allows the fitting to be performed requiring only minimal intervention from a specialist, such as a dentist or the like. In particular, once scanning has been performed, which can typically be achieved in any of a number of dental facilities, the apparatus can be manufactured remotely, and then supplied to the user in a finished state. This is in contrast to traditional dental appliance fitting techniques, which typically require intervention by dentists at a number of different stages, for example in creating moulds of the ultimate user's teeth, preliminary fitting, customisation, or the like, which adds significantly to the overall cost and inconvenience of obtaining an insert. By contrast the above described process can be performed largely remotely and is therefore cheaper and more convenient.

Following this, the method can include trimming and/or polishing the cured resin to ensure this is comfortable, before fitting the breathing assistance apparatus to the user to ensure this is suitable. In particular, the apparatus is typically checked for stability and comfort as well as to determine whether any breathing noises are noticeable in use. In particular, this will involve ensuring there is no rocking or lifting, that the apparatus does not rub on the gums, is not be too tight and does not cause pain to the teeth, muscles or jaw joint.

An alternative for remote manufacture of the insert is to use software to design the exact 3D file of the component required by filling the space between the STL file of the patient's teeth and the designed appliance. This structure can then be 3D printed from resins such as polyurethane or ethyl vinyl acetate.

Thus, in this case, the method includes manufacturing at least one insert using 3D printing from a 3D file. The insert is printed using Polyurethane or Ethyl Vinyl Acetate.

Alternatively, the method could include manufacturing at least one insert by thermoforming a thin sheet of a thermoplastic onto a jaw model, placing the thermoformed sheet in the body and filling any space between the body and thermoformed sheet with heated liquid, the liquid being at least one of the same and a similar material.

Figure 9:
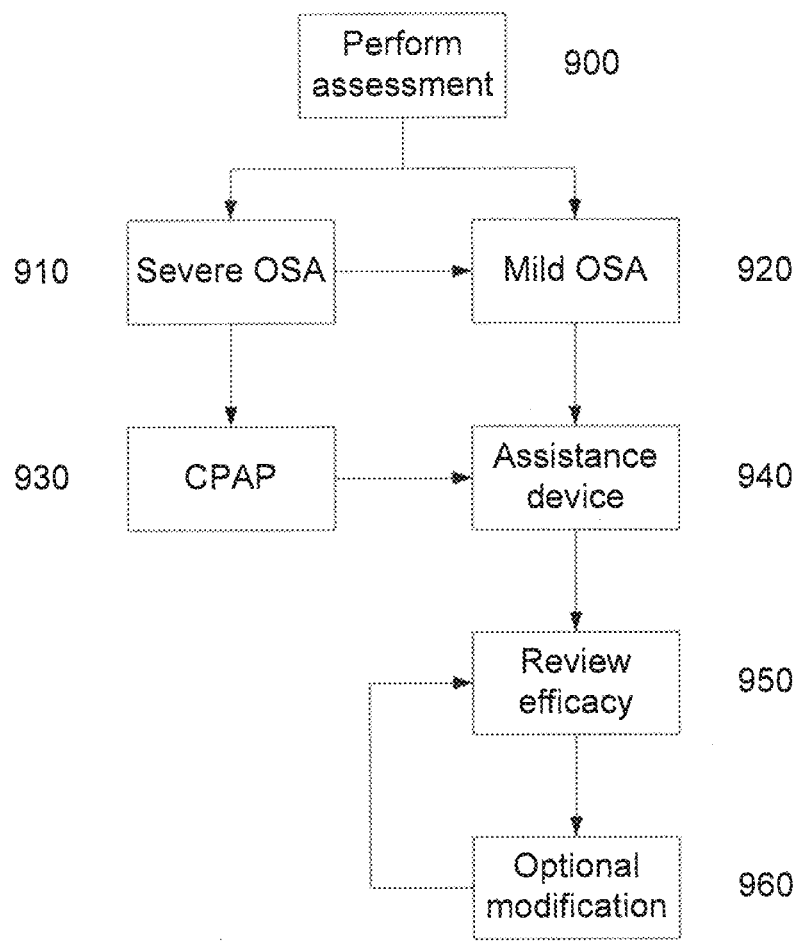

An example of the typical assessment process for a breathing assist device is shown in FIG. 9.

In this example, at step 900 the user typically undergoes preliminary assessment, such as a sleep study or the like, to ascertain whether the user has breathing difficulties while sleeping. This is typically used to determine whether the user has severe or mild/moderate OSA 910, 920. In the event that the user has severe OSA, they are typically referred for CPAP or other similar therapy, or undergo dietary and lifestyle modifications until they have only mild/moderate OSA.

In the event that the user has mild/moderate OSA, or is unsuitable for CPAP or similar therapy, then they may be referred for a breathing assistance apparatus at 940. This is then manufactured and fitted using the above described process, with use of the apparatus being reviewed at 950 following a period of use. This will typically involve assessing comfort, compliance and efficacy. This process typically includes use of a follow up questionnaire, sleep study, and Orofacial Pain Screening.

If it has been determines that the best form of treatment for the patient is a CPAP but the user cannot or does not like wearing a mask then the user may be fitted with an appliance and the appliance is the connected to a CPAP machine reducing leaks and eliminating the claustrophobic nature of face masks. In this instance, the tube from the CPAP machine can be connected directly to the opening 111, for example using a standard mask connector. In one example, the opening 111, can be configured to interface directly with commercially available CPAP mask connectors, allowing these to be coupled directly to the opening 111.

If the review is positive a PSG can be performed to examine efficacy in more detail. Alternatively, if the device is ineffective, the device can be modified at 9601, for example by titrating for more lower jaw advancement by replacing silicone, polyurethane or ethyl vinyl acetate inserts in a more advanced position. This can be continued until a positive result or a limit of advancement without causing pain is reached.

It will also be appreciated that the above described manufacturing techniques can be applied to any oral or dental appliance and are not restricted to the fitting of the breathing assistance apparatus described herein. In this example, the method would typically include determining a desired jaw position, obtaining shape information indicative of shape of the jaws at least in the desired jaw position and manufacturing the oral appliance at least in part using the shape information.

In the above description, the term "additive manufacturing" or "3D printing" is a process of making a three-dimensional solid object of virtually any shape from a digital model. 3D printing is achieved using an additive process, where successive layers of material are laid down in different shapes. 3D printing is also considered distinct from traditional machining techniques, which mostly rely on the removal of material by methods such as cutting or drilling (subtractive processes).

A 3D printer is a limited type of industrial robot that is capable of carrying out an additive process under computer control. To perform a print, the machine reads the design from an STL file and lays down successive layers of liquid, powder, paper or sheet material to build the model from a series of cross sections. These layers, which correspond to the virtual cross sections from the CAD model, are joined or automatically fused to create the final shape. The primary advantage of this technique is its ability to create almost any shape or geometric feature.

Machines, techniques and various parts made from additive manufacturing are now commercially available for various applications in polymers, metals, plaster and ceramics. These include architecture, construction (AEC), industrial design, automotive, aerospace, military, engineering, civil engineering, dental and medical industries, biotech (human tissue replacement), fashion, footwear, jewellery, eyewear, education, geographic information systems, food, and many other fields.

With respect to metals there are a number of variations to the generic term 'additive manufacturing' with each machine builder giving their own name to their particular version of the technology. These include wires using Electron Beam Freeform Fabrication (EBF3), granular metals using Direct metal laser sintering (DMLS), Electron-beam melting (EBM), Selective laser melting (SLM) and Selective laser sintering (SLS).

The devices for this invention have been manufactured using Electron Beam Melting using a machine from Arcam AB of Molndal, Sweden. This technique powerful electron beams (up to 3500 W) to build up layer-by-layer of metal powders using an 'Electron Beam Melting' (EBM) process. The EBM technology is capable of producing complex geometries from defined 3D CAD computer software at speeds up to 80 cm$^3$/hour. Each metal powder layer is melted to the exact geometry defined by the 3D CAD model. The electron beam is managed by electromagnetic coils rather than optics and moving mechanical parts, which is said to allow for very good beam control and extremely fast beam translation. EBM technology also provides a high energy beam which allows for high melting capacity and ultimately high productivity.

Although EBM was used for the device designs proposed herein, other additive manufacturing machines could be used to produce similar designs.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that the airway can also be incorporated into other forms of device, such as existing mandibular advancement devices, including appliances for elastic advancement, advancement with connectors, tongue retaining devices, bimaxillary fixed appliances, bimaxillary occusal appliances, or the like. The above described arrangement is therefore for the purposes of example and is not intended to be limiting.

The invention claimed is:

1. An apparatus for providing breathing assistance, the apparatus including a body for positioning within an oral cavity of a user, the body defining:
   at least one first opening for allowing airflow between lips of the user;
   two second openings provided in a posterior region of the oral cavity to allow air flow into and out of a posterior region of the oral cavity; and,
   two channels, each channel connecting one of the two second openings to the at least one first opening and each channel passing at least one of at least partially along the buccal cavity and at least partially between the teeth to thereby provide an airway for the user, the airway at least partially bypassing the nasal passage and configured to imitate a healthy nasal passage and pharyngeal space, and
   a connector for coupling the body to a mandibular repositioning device which is configured for engaging the teeth.

2. The apparatus according to claim 1, wherein for a device adapted to be used at rest, at least one of:
   a) each channel has a cross sectional area of at least one of:
      i) at least 10 mm$^2$;
      ii) at least 20 mm$^2$;
      iii) at least 30 mm$^2$;
      iv) at least 40 mm$^2$;
      v) at least 50 mm$^2$; and,
   b) at least one of the first opening and the second openings have a cross sectional area of at least one of:
      i) at least 50 mm$^2$;
      ii) at least 70 mm$^2$;
      iii) at least 90 mm$^2$;
      iv) at least 100 mm$^2$; and,
      v) at least 110 mm$^2$.

3. The apparatus according to claim 1, wherein the mandibular repositioning device is configured to allow for known increments for bringing the mandible forward.

4. The apparatus according to claim 1, wherein each channel includes:
   a first channel portion extending through the user's buccal cavity; and,
   a second channel portion in fluid communication with the first channel portion and extending between the user's maxillary and mandibular teeth, wherein the first channel portion has substantially semi-elliptical cross section and the second channel portion has a substantially rectangular cross section, the second channel portion extending laterally inwardly from the first channel portion and wherein at least one of the cross sectional shape and cross sectional area of at least one of the first and second channel portions varies from the first opening to the second opening.

5. The apparatus according to claim 1, wherein a shape and size of the channels varies in accordance with an anatomy of the oral cavity of the user.

6. The apparatus according to claim 1, wherein the body defines channel walls, and at least some of the channel walls have a thickness of at least one of:
   a) less than 0.5 mm; and,
   b) approximately 0.3 mm.

7. The apparatus according to claim 1, wherein the first opening is removably mounted to the body.

8. The apparatus according to claim 1, wherein the second openings are at least one of:
   a) angled inwardly at least one of:
      i) between 10° and 50°;
      ii) between 20° and 40°; and,
      iii) approximately 30°; and,
   b) positioned over the last or back tooth on each side of the top jaw.

9. The apparatus according to claim 1, wherein the body is at least one of:
   a) made of at least one of:
      i) metal;
      ii) titanium alloys;
      iii) high strength polymers; and,
      iv) cobalt chromium alloys; and, b) made using additive manufacturing;
c) coated with at least one of:
   i) a medical grade polymer;
   ii) a medical grade elastomer;
   iii) silicone;
   iv) polyurethane;
   v) epoxy; and,
   vi) parylene; and,
d) polished using at least one of mechanical and electrochemical polishing.

10. The apparatus according to claim 1, wherein the apparatus includes at least one insert, the insert being positioned at least partially between the user's teeth and the body in use, and wherein at least one of:
   a) the insert is customised for a user's teeth;
   b) the insert is at least one of removable and replaceable;
   c) a plurality of inserts are provided for each user, each insert being adapted to provide a different positioning of at least one of the body and the user's teeth;
   d) the insert is adapted to absorb impacts;
   e) the insert is made of at least one of:
      i) metals;
      ii) ceramics;
      iii) a polymer;
      iv) polyvinylsiloxane;
      v) polyurethane; and,
      vi) ethylvinylacetate.

11. The apparatus according to claim 1, wherein the apparatus includes at least one of:
   a) a filter for filtering air flowing through the apparatus;
   b) an exchanger for exchanging at least one of heat and moisture between inhaled and exhaled air; and,
   c) a valve for regulating air flow into and out of the apparatus.

12. The apparatus according to claim 1, wherein the body includes a lingual flange for engaging mandibular teeth to thereby maintain mandibular position.

13. A method for manufacturing a breathing assistance apparatus for a user, the method including using additive manufacturing to create a body for positioning within an oral cavity of the user, the body including:
   at least one first opening for allowing airflow between lips of the user;
   two second openings provided in a posterior region of the oral cavity to allow air flow into and out of a posterior region of the oral cavity;
   two channels, each channel connecting one of the two second openings to the at least one first opening and each channel passing at least one of at least partially along the buccal cavity and at least partially between the teeth to thereby provide an airway for the user, the airway at least partially bypassing the nasal passage and configured to imitate a healthy nasal passage and pharyngeal space; and
   a connector for coupling the body to a mandibular repositioning device which is configured for engaging the teeth.

14. The method according to claim 13, wherein the body is made of at least one of:
   a) metal;
   b) titanium alloys;
   c) high strength polymers; and,
   d) cobalt chromium alloys.

15. The method according to claim 13, wherein the method includes applying a coating to the body.

16. The method according to claim 13, wherein the method includes polishing at least part of the body using at least one of mechanical and electrochemical polishing.

17. The method according to claim 13, wherein the method includes:
   obtaining shape information indicative of a shape of the user's oral cavity; and,
   manufacturing the breathing assist apparatus using the shape information.

18. The method according to claim 17, wherein the method includes deriving the shape information from at least one of:
   a) an impression;
   b) a series of photos;
   c) a scan;
   d) a CT scan;
   e) a 3D scan of the user's teeth; and
   f) cone beam imaging; and,
   g) series of photos of the patients mouth or impression taken with a smart phone and the photos are then loaded into a software program to derive a 3D image including an STL file.

19. The method according to claim 17, wherein the shape information includes dimensions of the oral cavity of the user.

20. The method according to claim 17, wherein the method includes:
   selecting one of a number of standard bodies in accordance with the shape information; and,
   using the shape information, at least one of:
   i) modifying the selected standard body; and,
   ii) creating at least one insert.

21. The method according to claim 20, wherein the method includes:
   obtaining template data representing a body design;
   modifying the body design using the information derived from the scan;
   generating modified template data using the modified body design, wherein the modified template data is in the form of a print file for use in an additive manufacturing machine; and,
   manufacturing the body using the modified template data.

* * * * *